(12) United States Patent
Lohse et al.

(10) Patent No.: US 10,648,970 B2
(45) Date of Patent: May 12, 2020

(54) METHOD FOR EVALUATION OF TARGET IN HISTOLOGICAL SAMPLE

(71) Applicant: DAKO DENMARK A/S, Glostrup (DK)

(72) Inventors: Jesper Lohse, Herlev (DK); Kristian Jensen, Ringsted (DK); Rikke Malene Krusenst Jerna-Hafstrom, Birkerød (DK); Kirsten Damgaard Hoff, Måløv (DK); Lars Christian Jacobsen, Copenhagen (DK)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 221 days.

(21) Appl. No.: 14/356,735

(22) PCT Filed: Nov. 8, 2012

(86) PCT No.: PCT/DK2012/000119
§ 371 (c)(1),
(2) Date: May 7, 2014

(87) PCT Pub. No.: WO2013/068011
PCT Pub. Date: May 16, 2013

(65) Prior Publication Data
US 2014/0315218 A1  Oct. 23, 2014

Related U.S. Application Data

(60) Provisional application No. 61/556,916, filed on Nov. 8, 2011.

(30) Foreign Application Priority Data

Nov. 8, 2011  (WO) ............... PCT/DK2011/000131

(51) Int. Cl.
*G01N 33/53*  (2006.01)
*G01N 33/68*  (2006.01)
*G01N 33/58*  (2006.01)

(52) U.S. Cl.
CPC ......... *G01N 33/5308* (2013.01); *G01N 33/58* (2013.01); *G01N 33/6854* (2013.01)

(58) Field of Classification Search
None
See application file for complete search history.

(56) References Cited

U.S. PATENT DOCUMENTS

| 4,743,542 | A | * | 5/1988 | Graham et al. | ............. 435/7.94 |
| 5,366,859 | A | * | 11/1994 | Miyoshi et al. | .................. 435/5 |
| 6,746,848 | B2 | * | 6/2004 | Smith | ...................... G01N 1/30 |
| | | | | | 435/7.21 |
| 7,771,958 | B2 | * | 8/2010 | Bacus et al. | .................. 435/7.23 |
| 2009/0053743 | A1 | * | 2/2009 | Link et al. | .................... 435/7.93 |
| 2010/0285467 | A1 | | 11/2010 | Lohse et al. | |

FOREIGN PATENT DOCUMENTS

| CN | 102313810 | | 2/2012 | |
| WO | WO 9324838 | A1 * | 12/1993 | ............. G01N 3/566 |
| WO | WO-2007023390 | A2 * | 3/2007 | ......... A61K 49/0041 |
| WO | WO 2009/026168 | | 2/2009 | |
| WO | WO 2010094284 | A1 * | 8/2010 | ........... C08G 63/672 |
| WO | WO 2010/141249 | | 12/2010 | |
| WO | WO 2011047680 | A1 * | 4/2011 | ....... G01N 33/54306 |

OTHER PUBLICATIONS

Gosling, A Decade of Development in Immunoassay Methodology, Clin. Chem. 36/8, 1408-1427 (1990).*
M. Oellerich, "Enzyme Immunoassays in Clinical Chemistry: Present Status and Trends," J. Clin. Chem. Clin. Biochem., vol. 18, pp. 197-208 (1980).
M. Oellerich, "Enzyme-Immunoassy: A Review." J. Clin. Chem: Clin. Biochem., vol. 22, pp. 895-904 (1984).
International Search Report for International Patent Application No. PCT/DK2012/000119, dated Jan. 28, 2013.
G. Bradley, "Sex-Dependent and Independent Expression of the P-Glycoprotein Isoforms in Chinese Hamster," Journal of Cellular Physiology, vol. 145, No. 3, pp. 398-408, (1990).

* cited by examiner

*Primary Examiner* — Andrea S Grossman

(57) ABSTRACT

The present invention lies in the field of visualization and quantification of immobilized targets in samples using immunochemical means. In particular, the invention relates to a method and reagents for detection, visualization and quantification of a molecular target in immunostained histological samples using particular compositions of the target specific binding agent. Methods and compositions of the invention are suitable for any assay that uses a target visualization system in histological samples based on detection of the target by the target specific binding agent. The methods and compositions are useful for evaluation of targets that are biomarkers of diseases in medical diagnostic.

20 Claims, 2 Drawing Sheets

METHOD FOR EVALUATION OF TARGET IN HISTOLOGICAL SAMPLE

CROSS REFERENCES TO RELATED APPLICATION

This application is a national stage filing under 35 U.S.C. § 371 of International Application No. PCT/DK2012/000119, filed Nov. 8, 2012, in English and designating the United States of America, which is based on and claims the benefit of priority from U.S. Provisional Application No. 61/555,916, filed Nov. 8, 2011, and claims benefit to International Application No. PCT/DK2011/000131, filed Nov. 8, 2011, all of which are incorporated herein by reference.

FIELD OF THE INVENTION

The present invention lies in the field of visualization and quantification of immobilized targets in samples using immunochemical means. In particular, the invention relates to a method and reagents for detection, visualization and quantification of a molecular target in immunostained histological samples using particular compositions of the target specific binding agent. Methods and compositions of the invention are suitable for any assay that uses a target visualization system in histological samples based on detection of the target by the target specific binding agent. The methods and compositions are useful for evaluation of targets that are biomarkers of diseases in medical diagnostic.

BACKGROUND OF THE INVENTION

In the field of immunohistochemistry, IHC, biological targets of interest are typically stained with enzymatically generated dyes. However, most of today's IHC enzymatic systems have a limited usability of for target visualization due to restricted sensitivity: if a target is of very low abundance, the amount of deposited dye remains undetectable. Likewise, there is an upper detection limit above which a further dye deposition does not lead to detectably more intense stains. Using lower concentration of reagents, the upper detection limit may be compromised to allow differentiation between high and very high abundance targets; however this also leads to an increase of the lower detection limit, i.e. the loss in sensitivity of detection. Thus, most of the today's systems have a limited dynamic range of detection. Further, differences in sensitivity between different visualization systems from same or different vendors makes comparison the staining results difficult.

A further challenge is quantification of immunochemically stained targets due to the dye deposition is not a linear function of target concentration. Around the baseline of detection limit the intensity increases rapidly as a direct function of target concentration (as the going from no detectable signal to a signal, even of a low strength, represents an infinite increase. Conversely, close to the upper detection limit, even a large increase in target concentration will lead to virtually no perceptible increase in the already intense signal.

A further complication arises from the fact that no internationally recognized standards exist, and invariable reference samples are difficult to prepare. Even serial sections of the same tissue sample usually exhibit biological variation. Immortal cell lines might in principle provide the infinite reference material, however differences in cultivation conditions, cell cycle circles and biological variation will also in this case lead to some batch to batch variation in target expression. Glass slides chemically modified with peptides or proteins may be used as surrogate targets, however comparison to tissue samples is not straight forwards.

Thus there is a need for standardized quantitative detection of immobilized targets in biological samples.

Recently described methods of immunochemical staining of immobilized targets in biological samples, including histological samples, (WO2010094284, WO2010094283, WO201047680, WO2012143010) provide a visualization system characterized by an extreme sensitivity, such as single units of the target can be visualized and detected, which also allows a precise quantification of the target (as described in WO2012075028 WO2012062318), as the amount of deposited dye is in a linear correlation with the target expression. However, the latter visualization methods due to their extreme sensitivity, may in some cases have disadvantages, e.g. the methods are best applicable for visualization of a sub-fraction of a target in the sample, but not the whole expression range. This disadvantage may be an obstacle for broad use of the methods for visualization of targets in histological samples, especially when robustness of the procedure and reproducibility of the results are concerned. Further, the precise quantification of a target according to the methods may be laborious. The present invention solves the latter mentioned problems.

SUMMARY OF INVENTION

Use of lately developed reagents and methods allowing the detection of all or substantially all target units in histological samples, e.g. such as described in WO2010094284, WO2010094283, WO201047680 or WO2012143010, while having advantages with immunochemical staining of targets present in the samples at low to medium expressions levels, may also be associated with such drawbacks as overstaining of samples with targets present at abundant levels. It may be difficult to evaluate quantify and distribution of abundant targets in the samples and compare different histological samples comprising the same target. To reduce the target-specific signal in such samples, these methods utilize very low amounts of target-specific detecting agents, such target-specific binding agents, e.g. antibody reagents. This approach allows reducing the target-specific signal, but it also makes the detection of the target vulnerable to different conditions and results of the evaluation of target not fully reliable, especially, when the precision of the evaluation is crucial, e.g. in medical diagnostics.

The present invention relates to a method for detection, visualization and quantification of targets in samples, in particular, molecular targets, such as biological markers of diseases, where the target is immobilized on or within a solid support. In particular, the invention relates to detection and evaluation of the target expression in histological samples. The present invention solves technical problems of the mentioned extremely sensitive and powerful detection systems employing immunostaining of targets in histological samples. In particular it solves the problem of generation of excessive target-specific signal produced due to super powerful amplification of the signal, and the problem of insufficient robustness of the systems due to necessity of using very low amounts of target-specific detection agents, by providing a method and reagents that make these detection systems robust without compromising their advantages.

Thus, in one aspect the invention relates to a method for detecting a target in a target site in a histological sample, wherein the target site comprises a binding partner for a binding agent, comprising a) Incubating the sample presumably comprising the target in one or more target sites in an incubation medium comprising a binding agent which is capable of specifically binding to the binding partner comprised in said one or more target sites, wherein the amount of the binding agent in the incubation medium is sufficient to bind to substantially all units of the binding partner present in the sample, and wherein the binding agent is characterized in that it comprises first binding molecules and second binding molecules, wherein the first binding molecules comprise a binding part and a detectable part, and the second binding molecules comprise a binding part, wherein the binding part of both first and second binding molecules is capable of specifically binding to the binding partner and competing for said binding, and wherein the second binding molecules do not comprise a part that is substantially identical to the detectable part of the first binding molecules;

(b) Detecting the detectable part of the first binding molecules in the sample, thereby detecting the target in the target sites.

In another aspect the invention relates to a kit-of-parts comprising a composition comprising a binding agent which is capable of specifically binding to the binding partner comprised in said one or more target sites, wherein the amount of the binding agent is sufficient to bind to substantially all units of the binding partner present in the sample, and wherein the binding agent is characterized in that it comprises first binding molecules and second binding molecules, wherein the first binding molecules comprise a binding part and a detectable part, and the second binding molecules comprise a binding part, wherein the binding part of both first and second binding molecules is capable of specifically binding to the binding partner and competing for said binding, and wherein the second binding molecules do not comprise a part that is substantially identical to the detectable part of the first binding, molecules.

In another aspect the invention relates to an assay for evaluation of a target in a histological sample, comprising a step of detection of the target in a histological sample according to the method of invention.

One advantage of the invention is that the methods and kits may be implemented to any method for visualization targets in histological samples based on use of target-specific binding agents for detection and visualization of the target.

Another advantage is that the methods of the invention allow identifying and counting single units of a target in a histological sample and, allow determining both the absolute or relative quantity of the target repeatedly precisely and independently of the level of target expression. This of particular advantage for quantification of diagnostic or therapeutic targets such as growth factor receptors, e.g. Her2 or the like, and thus, utility of the present methods in diagnostic and therapeutic applications cannot be overrated.

The invention allows obtaining the target-specific signal of any desirable intensity which makes its use in combination with new powerful target visualization methods important for successful implementing these visualization methods in medical diagnostics, which standards and scoring systems have been developed based on evaluation of target-specific signals produced in histological samples by much less sensitive and capable visualization systems.

Suitability of the invention for both manual and automatic evaluation of the quantity of a target in samples is an additional valuable feature.

The methods are also applicable to any sample comprising a target immobilized on/within a solid support that is detectable by a binding agent that has affinity to that target. Thus, virtually any immobilized target which has an affinity binding partner, such as e.g. a chemical and biological molecule, particle, microorganism, etc, can be detected and precisely quantified by the methods of the invention.

DETAILED DESCRIPTION OF INVENTION

1. Method

Figure 1:
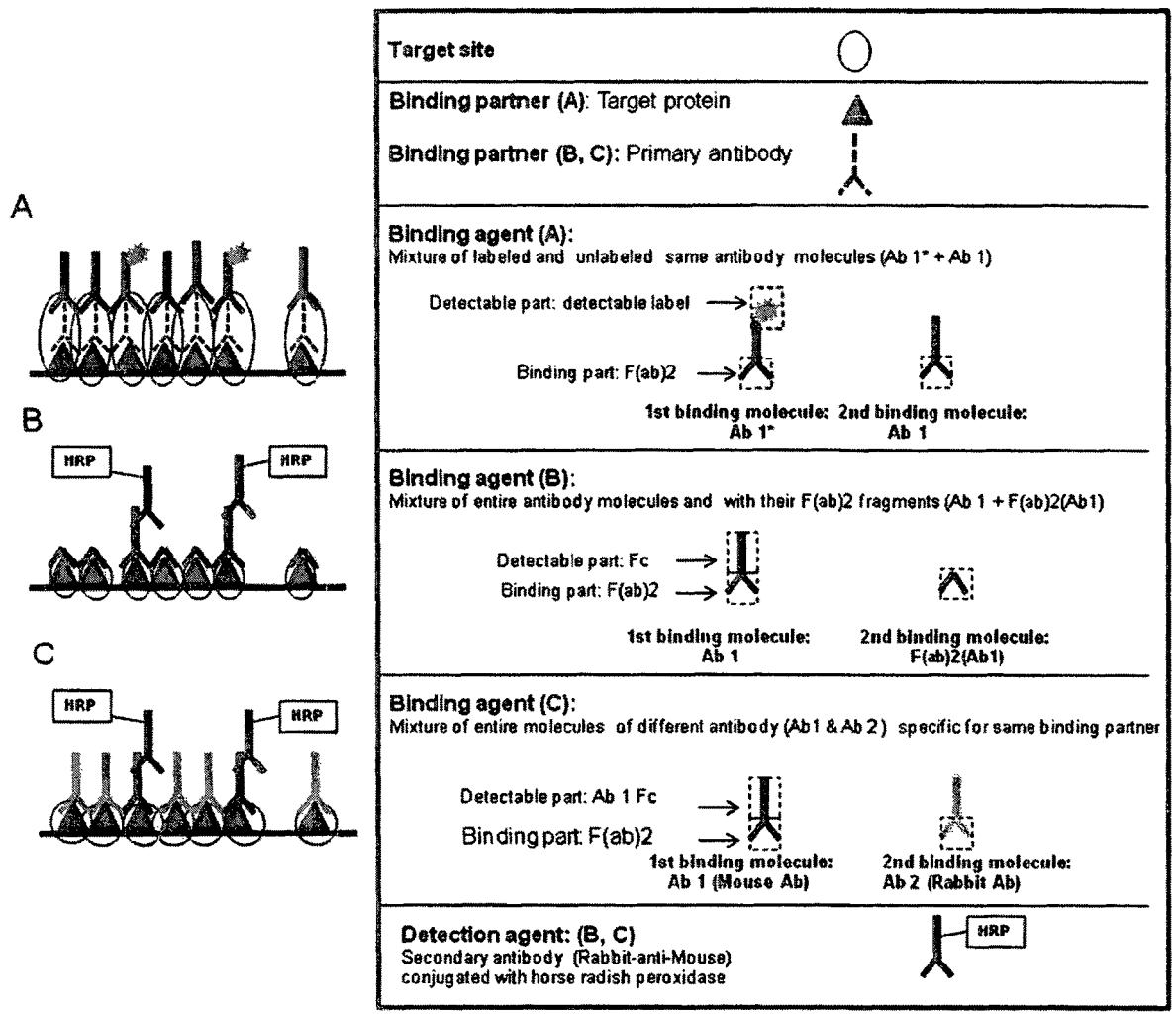
FIG. 1 demonstrates selected non-limiting embodiments of the invention.

One aspect of the invention relates to a method for detecting a target in a target site in a histological sample, wherein the target site comprises a binding partner for a binding agent, comprising a) Incubating the sample presumably comprising the target in one or more target sites in an incubation medium comprising a binding agent which is capable of specifically binding to the binding partner comprised in said one or more target sites, wherein the amount of the binding agent is sufficient to bind to substantially all units of the binding partner present in the sample, and wherein the binding agent is characterized in that it comprises first binding molecules and second binding molecules, wherein the first binding molecules comprise a binding part and a detectable part, and the second binding molecules comprise a binding part, wherein the binding part of both first and second binding molecules is capable of specifically binding to the binding partner and competing for said binding, and wherein the second binding molecules do not comprise a part that is substantially identical to the detectable part of the first binding molecules;

(b) Detecting the detectable part of the first binding molecules in the sample, thereby detecting the target in the target sites;

Another aspect of the invention relates to an assay for evaluation of a target in a sample, in particular, a histological sample, comprising a step of detection of the target in a target site of the sample according to the method of the invention.

Different embodiments of the invention as stated above are described below and illustrated by non-limiting working examples described in the section EXAMPLES.

Sample

The term "sample" means a representative part or a single item from a larger whole or group, an amount or portion of a matter or object that supposedly contains a target of interest, e.g. a portion or amount of biological material comprising a target molecule, particle, structure to be analyzed, e.g. a body tissue sample, such as a biopsy sample, a blood sample, etc. A typical sample shows what the rest of the matter or object is or should be like. In one preferred embodiment a sample of the invention is a histological sample.

Non-limiting examples of a histological sample in the context of the present invention may be the following:
1. a sample comprising suspended cells and/or cells debris, e.g. blood sample, suspension of cloned cells, body tissue homogenate, etc;
2. a sample comprising of intact or damaged cells of an animal body, a body tissue, smear or fluid or a sample of a tumor, e.g. a biopsy sample; It may be a fresh tissue sample or preserved tissue sample, e.g. a formalin fixed paraffin embedded tissue sample;
3. a sample comprising a living organism, e.g. a sample of a medium comprising an animal, plant, bacterium, fungi, etc;
4. a sample comprising viral particles, debris thereof, or viral products, e.g., a body smear comprising viral nucleic acids, proteins, peptides, etc;
5. a sample comprising a cell organelle(s);
6. a sample comprising natural or recombinant biological molecules, e.g. blood plasma sample, conditioned cell culture media, etc.
7. a sample comprising plant cells or derbies thereof.

The invention relates to samples comprising an immobilized target, i.e. to samples, where the target is prevented from freedom of movement during a detection procedure of the present invention, e.g. samples, where the target motion is substantially reduced or eliminate by mechanical or chemical means, as e.g. in case of samples or targets attached to or within a certain support or medium. Thus, a sample comprising single individual units of a target of interest may in one embodiment be immobilized onto a solid support before the detection procedure, e.g. a solid body tissue sample immobilized on a glass slide. Examples of samples comprising immobilized targets of the invention include but not limited to body tissue samples immobilized on glass or plastic slides; or samples comprising biological or chemical molecules immobilized onto membranes, etc. A target of a sample in these embodiments may be immobilized either within the sample, e.g. a protein fixed within a tissue sample, or is immobilized on the surface or within certain material, such as e.g. a portion of a solid material or a gel such as a nitrocellulose membrane, etc. In one embodiment the solid support may be a three-dimensional structure, e.g. a collagen or agar block or the like. In this embodiment a target, e.g. molecule or particle may be immobilized within the structure. The term "solid support" means a piece of any material that is insoluble under conditions of the procedures according to the invention, e.g. it may be a nitrocellulose membrane, glass slide etc. Examples of supports suitable for immobilizing samples and/or targets include but not limited to synthetic polymer supports, such as polystyrene, polypropylene, substituted polystyrene, e.g., aminated or carboxylated polystyrene; polyacrylamides; polyamides; polyvinylchloride; glass; agarose; nitrocellulose; nylon; polyvinylidenedifluoride; surface-modified nylon, etc. The invention relates to a solid support that is chemically inert under conditions described herein, i.e. the chosen support may not have any major influence on the results of detection by the method. Accordingly, any such inert support suitable for immobilizing a sample or target fitting the chosen assay format, e.g. for IHC, ELISA, blotting etc, may be selected.

The invention is also applicable to environmental samples, e.g. a sample of a soil or a sample of a spillage; food samples; samples of a library of organic molecules; samples of warfare.

In one embodiment the invention relate to a sample (as any of the above) that does not comprise the target, i.e. a negative control sample. In another embodiment, the invention relate to a sample that supposedly comprise the target, i.e. a test sample. In one embodiment, the invention relates to a sample comprising a predetermined amount of the target of interest, i.e. a reference sample. In one embodiment, the reference sample is a histological sample, e.g. a sample comprising cells expressing certain levels of the target of interest, e.g. a target protein or target nucleic acid. It may be preferred that the reference sample is treated or pretreated in the same way as the test sample and the amount of target in the reference sample is determined according to the method of the invention.

Target

The term "target" means in the present content an object of interest supposedly present in a sample that can be characterized by particular physical and/or functional features. In the context of the invention the term "target" relates to the whole pool of substantially identical entities of that object, not to a single entity of that object in a sample; in samples where a target is represented by the only single unit, this only single target unit is understood as target (i.e. the whole target pool). The term "substantially identical" in the present context means that all or substantially all single entities of the target in a sample possess one or more features that make them recognizable as the target. For example, the target may be a particular protein including all molecules of that particular protein in a sample; a target of the invention may be a particular molecular complex or structure including substantially all objects of the sample that comprise that particular molecular complex or molecular structure; another example of a target of the invention may be a viral particle or a bacterium, wherein total population of that viral particles or that bacteria of the sample is the target.

Biological objects such as molecules, molecular complexes, molecular structures, particles or organisms which are associated with features that are characteristic for a particular cell type, tissue, cellular structure, physiological condition, etc., are termed "biological markers" of that particular cell type, tissue, cellular structure, or physiological condition. Non-limited examples of such biological markers, that may be targets of the invention, include but not-limited to particular nucleotide sequences, proteins or other biological molecules, e.g. carbohydrates or lipids, chromosomal or membrane structures, viruses, bacteria, microorganisms etc. In some embodiments of the invention, the term "target" is used interchangeable with the term "biological marker" and relates to a molecule, molecular complex, structure or particle that is characteristic for a particular cell type, tissue, physiologic condition, etc, wherein the total population of any of the latter biological markers in the test sample is considered to be the target.

In one embodiment, the target may be a protein, e.g. a cellular membrane receptor or a cytoplasmic protein, in another embodiment the target may be a nucleic acid, e.g. a cytoplasmic nucleic acid. Derivatives of any latter mentioned targets, e.g. fragments, precursors, mutants of target proteins or nucleic acids, etc. may also be targets in some embodiments of the invention.

Among targets contained in chemical and environmental samples may be different pollutants, toxins, warfare substances, members of molecular libraries, industrial noxious waste compounds, etc.

In one embodiment the invention relates to single units of targets that in different embodiments may be represented by whole single molecules of targets or fragments of said single molecules of targets, or single molecular structures, particles, etc.

By the term "single unit of target" is meant a single quantity of target that can be regarded as the whole in calculation and that may, in some embodiments, possess a particular function (which is also the function of the target as whole). The term "single" in the present content means one target unit as opposed to or in contrast with many, e.g. one protein molecule of the target protein, i.e. one molecule of plurality molecules of the same kind.

In some embodiments the invention relates to a single unit of target, wherein said single unit is a part of a target molecule, e.g. an epitope, a structural or functional domain of a protein molecule, or the like.

In one preferred embodiment, the target is a biological marker related to cancer, e.g. nucleic acids and polypeptides of hormones and growth factors and their receptors, cell adhesion molecules signal transduction molecules, cell cycle regulation molecules, etc, e.g. genes, RNAs and proteins of the group including growth factors PDGF, VEGF, TGF, HGF or EGF, their receptors and the pathway related molecules, genes and their products relating to signal transduction pathways, e.g. the JAK/STAT pathway or Akt1/PKB cell survival pathway, or 5-FU pathway, estrogen receptor ER and its gene (ERS1), etc. In one preferred embodiment, the invention relates to nucleic acid sequences, such as the genes, RNA molecules, and protein molecules of the ErbB family of receptors. Protein molecules, aggregates of said molecules, genes, RNAs, fragments of genes, proteins and RNAs, structural and functional domains thereof are contemplated as targets of the invention.

The invention allows detecting, visualizing and quantifying single individual units of a target present in a histological sample in a broad dynamic range, including quantifying single target units. Two or more different targets may be visualized in one or the same sample, e.g. a protein target and nucleic acid target, or two or more different protein targets, or two or more different nucleic acid targets, etc.

According to the invention immobilized target units are located in discrete target sites of a sample. The target site may comprise a single target unit or it may comprise a single target unit which is directly or indirectly associated with one or more substances, e.g. a target unit directly or indirectly bound to one or more substances, e.g. a unit of the target bound to a primary antibody molecule, or primary antibody bound to a hapten conjugated with a unit of the target, or a secondary antibody bound to either of these primary antibodies, or the like. Targets units located in target sites of the sample or substances associated with the target units, that can be detected by the target unit or the substance-specific binding agents of the invention are termed herein "binding partners" of corresponding binding agents. In one embodiment, the invention relates targets, and/or substances associated with targets that are the first members of specific binding pairs, wherein the second members are the target or substance (correspondingly) specific binding agents, i.e. the targets and/or substances are specific binding partners for the corresponding binding agents.

Binding Agent

The term "binding agent" in context of the present invention relates to substances that can specifically bind to another substance present in a test sample such as its binding partner present in a target site of a sample; preferably, the binding partner makes a specific binding pair with its binding partner in the sample, wherein said specific binding pair can be characterized by a particular value of the dissociation constant (Kd). A number of different specific binding pairs are known in the art, these are the pairs of two different molecules which are capable of specific binding to each other. Non-limiting examples of specific binding pairs suitable for the invention are discussed below.

In one embodiment the binding agent may be a member of a specific binding pair with the target in a sample. In another embodiment, the binding agent may be a member of a specific binding pair with a substance which is directly or indirectly associated with the target in a sample.

In particular, binding agents of the invention are capable of directly and specifically binding to their binding partners present in target sites of the sample. The term "specifically binding" means, in one embodiment, that the binding agent-binding partner binding has affinity defined by the corresponding Kd value. Some examples of affinity binding illustrating the latter may be the primary antibody-antigen binding; in another embodiment, "specifically binding" may relate to binding of two complementary nucleotide sequences under stringency conditions discussed below.

The binding agent of the invention is represented by two populations of binding molecules termed herein as first binding molecules and second binding molecules. According to the invention, both first and second binding molecules are capable of specific and direct binding to the same binding partner present in a binding site of the sample, wherein the binding partner is a target or a substance associated with the target in a target site of the sample. According to the invention, the first and the second binding molecules are capable of inhibiting each other specific binding to the binding partner. This means that the first binding molecules and the second binding molecules comprised in one binding agent has either affinity to the same single unit of the binding partner in the sample (e.g. the same epitope or hapten, or the like) and competitively inhibit each other binding to said binding partner, or they have affinity to different single units of the binding partner (e.g. different epitopes, or haptens or the like) which different single units are located within the binding partner molecule so, that binding of one binding molecule to the first of the different single units is capable of preventing binding of the other binding molecule to the second of the different single units, e.g. for the reasons of sterical hindrance. The term "inhibiting binding" means in the present content one binding molecule of the binding agent has a capability of reducing another binding molecule of the binding agent to interact with the single unit of the binding partner (or single unit of a substance that is associated with the target) and form a specific binding pair with it. Accordingly, the first binding molecule and the second binding molecule in one embodiment have affinity to the same single unit (e.g. same epitope) of same binding partner, in another embodiment the first binding molecule has affinity to a first single unit of a binding partner (e.g. first epitope) and the second binding molecule has affinity to another single unit of the same binding partner (e.g. a second epitope), wherein the first single unit and the second single unit are located within the binding partner so that binding to the first single unit prevents binding to the second binding unit and vice versa. The latter is also valid in embodiments when the single unit of a binding partner is a whole single molecule, structure, particle etc.; then, in one embodiment, the first and second binding molecules can prevent each other binding to said molecule, structure, particle etc.; in another embodiment the binding molecules can prevent each other binding to two individual single units of said partner.

According to the invention, first and second binding molecules comprised in the binding agent are similar in that they both comprise a part ("binding part") that has is capable of specific binding an individual single unit of the binding partner present in a target site of the invention. This part may be structurally identical in both molecules. In other embodiments, the binding parts of the first and second binding molecules may be structurally different. Accordingly, affinity of binding of the first binding molecule to the binding partner may have first Kd value and binding of the second binding molecules to the same binding partner may have second Kd value, wherein the first and second Kd values differs from each other. However, for both binding molecules the binding part defines the function of the binding molecule as the member of a specific binding pair with the same binding partner.

Both the first and the second binding molecules comprised in the same binding agent may further comprise a part that may have a function as detectable label, i.e. be detectable by application of the appropriate detection means. However, in any embodiment the second binding molecules may not comprise a part that is substantially identical to the detectable part of the first binding molecules. The term "substantially identical" means that the detectable part of the second binding molecules may not be detected by the same detection means as the detectable part of the first binding molecules.

The detectable part of the first binding molecule may be any detectable substance available in the art, e.g. a chromogenic fluorescent or luminescent label (collectively termed "optically detectable" labels), radioactive, magnetic label, a hapten, an enzyme, an enzyme substrate, etc. Some non-limiting particular examples of suitable labels are discussed below.

The detectable part, in one embodiment of the invention, may be a part of the same binding molecule, e.g. the Fc fragment of an antibody; accordingly, in such embodiment the second binding molecule comprised in the same binding agent may not comprise the Fc fragment of the same antibody, while it may comprise the antigen binding part (such as e.g. the F(ab) fragment) of this antibody. The latter means that in one embodiment where the binding agent comprises two different antibodies specific for the same antigen or epitope (e.g. a first and second antibody derived from different host species), the first antibody is the first binding molecule and the second antibody is the second binding molecule; the Fc region of the first antibodies is the detectable part of the binding agent of the invention. The Fc region of the second antibody is not the detectable part in the context of the present invention.

Another example illustrating the above may be the binding agent comprising two nucleic acid probes (first and second binding molecules), each comprising a nucleotide sequence capable of hybridizing under similar stringency conditions with the same target nucleic acid (i.e. the binding partner) located in the target sites of a sample. Only one of the probes, the first binding molecule, is to comprise the detectable part, which may be a detectable substance linked to the binding part, such any of the described herein, or it may be a nucleotide sequence that is not capable of hybridizing with the target sequence under the same condition. Another probe, the second binding agent, may not comprise the same detectable substance or the same nucleic acid sequence, while it may comprise another nucleotide substance which is not "detectable" in the context of the present invention.

Members of specific binding pairs suitable for use in practicing the invention may be of the immune or non-immune type.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Immune specific binding pairs may be exemplified by antibody-antibody systems or hapten-anti-hapten systems. In one embodiment the immune specific binding pair of the invention may be an antibody-antibody binding pair comprising two or more antibody molecules having affinity to each other, for example a primary antibody and secondary antibody pair, wherein the primary antibody represents the binding partner and the secondary antibody represents the binding agent; Antibody systems comprising 3 or 4, or more antibody members may also be used. In other embodiments of the invention the immune binding pair may be represented by a hapten-anti-hapten system. In such embodiments the binding agent may comprise the first binding molecule which a conjugate comprising a molecule having affinity to a binding partner in a target site (e.g. a target) and linked to a hapten, e.g. a primary antibody-hapten conjugate or nucleic acid sequence-hapten conjugate, and the second binding agent which is the same antibody molecule or the same a nucleic acid sequence, both without the hapten. The hapten (i.e. the detectable part of the first binding molecule) may be then detected by a detection agent specific for the hapten (e.g. indirectly with use of the anti-hapten antibody, or directly via microscopic observation, if the hapten is a visually detectable substance, e.g. a fluorescent label).

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include Fluorescein (FITC), 2,4-Dinitrophenol (DNP), myc Digoxigenin (DIG), tyrosine, nitrotyrosine biotin and dyes. e.g. tetramethylrhodamine, Texas Red, dansyl, Alexa Fluor 488, BODIPY FL, lucifer yellow and Alexa Fluor 405/Cascade Blue fluorophores, Haptens are described in US20080305497 may also be used for the purposes of the invention.

The term "antibody", as used herein, designates an immunoglobulin or a part thereof, and includes any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR-grafted antibodies. The antigen binding part of an antibody includes any antibody fragment which can still bind antigen, for example, an Fab, F(ab')$_2$, Fv, scFv, or fragments or derivatives thereof, e.g. recombinant molecules, etc. The origin of the antibody is defined by the genomic sequence irrespective of the method of production.

Primary antibody, in context of the present invention, refers to an antigen binding agent, e.g. a whole primary antibody molecule, a fragment or a derivative of said molecule, e.g. a conjugate comprising a primary antibody or a polymerized primary antibody, that specifically binds to its antigen, e.g. target molecule or another single unit of a target, hapten, etc. In some embodiments, a primary antibody may be a bivalent antibody which is capable of binding to two (or more) single individual units of different targets, e.g. an antibody that is capable of binding to a receptor dimer, e.g. Her2/Her3 dimer. In this embodiment the single unit of a target according to the invention is a single Her2/Her3 dimer, and the target is a population of Her2/her3 dimers in a sample including all said dimers of the sample.

Secondary antibody, in context of the present invention, refers to a binding agent capable of specifically binding to the corresponding primary antibody. It may be a whole antibody molecule, a fragment or a derivative of said molecule, e.g. a conjugate comprising an antibody or a polymerized antibody, that have an antigen binding domain that specifically binds to the primary antibody.

Tertiary antibody, in context of the present invention, refers to an antibody capable of binding to the corresponding secondary antibody. It may be a whole antibody molecule, a fragment or a derivative of said molecule, e.g. a conjugate comprising an antibody or a polymerized antibody that comprise an antigen binding domain that specifically binds to a secondary antibody or a hapten linked to a secondary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments, any antibody (primary, secondary or tertiary) may be conjugated to a polymer. In some embodiments, 1-20 antibody molecules their fragments or derivatives, such as e.g. 5-15 molecules, 1-10, etc, may be conjugated with a polymer, e.g. 1, 2, 3, 4, 5, 6, 7, 8, 9 or 10 molecules per polymer.

Engineered antibodies including chimeric, CDR-grafted and artificially selected antibodies produced using phage display or alternative techniques mat be use as binding molecules comprised in the binding agent of the invention.

Antibodies comprised in binding agents or as detection agents of the invention may be produced by any of numerous methods well-known in the art e.g., according to Harlow and Lane, *Antibodies: a Laboratory Manual*, (1988) (Cold Spring Harbor Press, Cold Spring Harbor, N.Y.). Techniques for the preparation of recombinant antibody molecules are described in the above reference and a number of other references, e.g., EP 0623679; EP 0368684; and EP 0436597. Nucleic acids encoding antibodies may be isolated from a cDNA library. Nucleic acids encoding antibodies may be isolated from a phage library (see e.g. McCafferty at al. 1990, *Nature* 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse at al. 1993, *Nucl. Acid Res.* 21:2265). The antibodies used in the methods of the invention include humanized immunoglobulins (see U.S. Pat. No. 5,585,089, Jones at al. 1986, *Nature* 332:323). Antibodies of the invention may be altered any possible way, presuming that they retain their binding affinity, e.g., they may fused with an effector protein, toxin, label, etc. Methods of conjugation of antibody with different agents are well known in the art.

In one preferred embodiment, both binding molecules of the binding agent are or comprise an antibody or an antigen-binding portion of an antibody, and the binding partner is a molecule comprising the antigen, e.g. an antigenic entity, such as hapten or amino acid sequence or the like.

In one preferred embodiment of the invention, the detectable part of the first binding molecule is the Fc region of an antibody, a fragment or a derivative thereof; one embodiments, is of the same antibody as the binding part of the first binding molecule; in other embodiments, is of another antibody, i.e. of an antibody that has the antigen binding part different from the binding part of the first binding agent.

In one preferred embodiment, the first binding molecule is or comprises a primary antibody molecule, or a derivative thereof, specific for an epitope comprised in the binding partner, and the second binding molecule is selected from a molecule that comprises an antigen binding portion of said primary antibody, or a molecule that comprises an antigen binding portion of another antibody, wherein said another antibody is specific for the same epitope as said primary antibody, or is capable of inhibiting the first binding molecule binding to said epitope In another preferred embodiment, the binding agent comprises labeled and unlabeled molecules comprising an antigen binding portion of the same antibody, such as labeled and unlabeled normal or derivatized molecules of a primary antibody, labeled and unlabeled normal or derivatized antibody molecules of a secondary antibody, or labeled and unlabeled conjugate molecules comprising normal or derivatized molecules of a primary or a or labeled and unlabeled conjugate molecules comprising normal or derivatized molecules of secondary antibody.

In one embodiment of the invention, the binding agent is represented by a first and a second binding molecules that comprise an antigen binding region of an antibody, such as a Fab region, e.g. F(ab)1 or F(ab)2 fragments of an antibody.

In one preferred embodiment, the binding part of the first binding molecule and the second binding molecule are or comprise the F(ab)2 fragment of the same primary antibody specific for an epitope comprised in the binding partner, or the F(ab)2 fragments of two different primary antibodies that are specific for the same epitope, or capable of inhibiting binding of the first binding molecules to the epitope.

In another preferred embodiment, the binding part of the first binding molecule and the binding part of the second binding molecule are or comprise the F(ab)2 fragments of the same secondary antibody or F(ab)2 fragments two different secondary antibodies that are specific for the same primary antibody.

In some embodiments the binding agent may be a composition comprising more than two different antibody molecules, e.g. 3, 4, 5, etc different antibody molecules. In this embodiment, one or more antibodies may be the first binding molecules and all the other antibody molecules comprised in the binding agent are representatives the population of the second binding molecules.

As mentioned, in some embodiments, the invention relates to binding agents that comprise first and second binding molecules that comprise the binding part which is a member of a non-immune specific binding pair with the binding partner in the target site, e.g. nucleotide sequences, or nucleic acid analog molecules. One preferred embodiment of the invention related to a binding agent that comprises the first and second binding molecules that are or comprise a nucleic acid or a nucleic acid analog, which binding partner is a nucleic acid in the sample.

A binding agent comprising a nucleic acid or nucleic acid analog molecule, e.g., a DNA molecule, an RNA molecule, a PNA molecule, etc., may be useful for the detection of nucleic acid targets. A binding agent that comprises the first and second binding molecules that are or comprise a nucleic acid sequence or a nucleic acid analog sequence, and the binding partner is a nucleotide sequence in the sample may be a preferred embodiment. Further, it may be preferred that the first and the second binding molecules comprising a nucleic acid sequence or a nucleic acid analog sequence, or the like, comprised in the binding part are capable of hybridizing with the same binding partner under same stringent conditions, such as low to medium stringent conditions. In some embodiment, the binding molecules may preferably hybridize with the partner nucleic acid in the sample under high stringency conditions.

Nucleic acid sequences used as binding agents for the purposes of the invention may be synthesized chemically or produced in recombinant cells. Both modes of production are well known in ht eart (see e.g. Sambrook et al. (1989) *Molecular Cloning: A Laboratory Manual; 2nd ed*. Cold Spring Harbor Press). In some embodiments, a nucleic acid binding agent may comprise a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the binding agent may comprise a locked nucleic acid (LNA) (Sorenson et al. 2003, *Chem. Commun.* 7(17):2130).

A nucleic acid binding agent, in some embodiments, may comprise at least one oligo- or at least one polynucleotide sequence that specifically hybridizes to a single unit of a target sequence in a biological sample, e.g. a single mRNA sequence, under specific conditions of stringency. The term "hybridization under stringent conditions," is used herein to describe conditions for hybridization under which nucleotide sequences that are significantly complementary to each other, such as at least 70%, at least 80%, at least 85-90% complementary, remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual, 2nd ed*. Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual,* 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

In other embodiments the invention may relate to binding agents comprising first and second binding molecules that comprise peptide sequences that are derived from non-antibody proteins, e.g. peptide sequences derived from nucleic acid binding domains of different proteins, ligands of different cellular and nuclear receptors and their derivatives. Some non-limiting examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain.

The binding part of the binding molecules of a binding agent of the invention may also be a small molecule which can bind specifically to certain structural units of large biological molecules.

As mentioned, the detectable part of the first binding agent may be or may comprise a detectable substance, e.g. a fluorescent label, hapten, enzyme, etc. Non-limiting hapten labels are described above. Non-limiting examples of fluorescent, luminescent, radioactive, chromogen or magnetic labels may be 5-(and 6)-carboxyfluorescein, 5- or 6-carboxyfluorescein, 6-(fluorescein)-5-(and 6)-carbox-amido hexanoic acid, fluorescein isothiocyanate, rhodamine, tetramethyirhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, DNP, digoxiginin, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor; magnetic particles or beads. Non-limiting examples of suitable enzyme labels may be horseradish peroxidase (HRP), alkaline phosphatase (AP), beta-galactosidase (GAL), glucose-6-phosphate dehydrogenase, beta-N-acetyl-glucosaminidase, ß-glucuronidase, invertase, xanthine oxidase, firefly luciferase, glucose oxidase (GO). In one preferred embodiment the first binding molecule may comprise HRP as the detectable part.

The amount of the binding agent used in the method according to the invention is predetermined so, that the first and second binding molecules of the binding agent together bind to substantially all units of their binding partner present in the sample. The term "substantially all" means that at the binding agent saturates at least 51% of the affinity binding sites of the sample (i.e. the sites where the corresponding binding partner is available for affinity binding), or more; preferably, more than 51% of the binding sites, such as up to about 66% of the sites; preferably, more than 60%, such as up to about 75% of the sites or more, for example up to about 80% of the sites, or up to about 90% of the sites or more. This means that the amount of the binding agent should be at least equal or, preferably, above of the Kd value of binding agent-binding partner complex in the sample, preferably, above of the Kd value, such as 10-1000% above of the value, or more. The Kd value of binding agent-binding partner complex may be defined for a mixture of first and second binding molecules or separately for each binding molecule following the corresponding instructions of the art, e.g. as exemplified herein in Example 1 or 2 for antibody binding agents.

The invention relates to a great variety of sample species, binding partner species, binding molecule species, various values of binding affinity between binding molecules of the binding agent ant their binding partner, according the amounts of the binding agent applied to a sample in different embodiments vary depending on the embodiment. Using common general knowledge the skilled in the art can select an appropriate binding agent molecules and determine their affinity to the binding partner of interest in the sample, and, thus, the amount of binding agent needed for every particular embodiment.

In one embodiment of the invention, the binding agent may contain an amount of the second binding molecules that is equal or, preferably, higher than the Kd of the second binding molecule-binding partner complex, such as 5-50% higher the Kd value, such as 10-100% higher, 20-200% higher, 30-300% higher, 40-400% higher, etc.

According to the invention a high amount of the binding agent comprising a mixture of first and second binding molecules (as any of the described above), wherein a portion of the second binding molecules is predetermined as above, has that advantage that it allows detecting a fractional sub-population of the target sites (comprising single target units) in the sample labeled with the detectable part of first binding molecules that is predetermined by the predetermined amount of the second binding agent in the binding agent mixture. Thus, the quantity of the corresponding binding target in the sample can be determined precisely and repeatedly. Non-limiting examples of practical use of the invention for evaluation of the amount of a target in a histological sample are described herein in EXAMPLES.

Incubation Media

According to the invention a sample supposedly comprising target sites of the invention is incubated in media comprising a binding agent of the invention. Incubating of the sample means maintaining the sample in incubation media for a period of time to allow a certain event happening, e.g. a binding event, a chemical reaction, etc. The term "incubation media" means in the present context an aqueous solution comprising compounds that allows the certain event happened, e.g. binding agent molecules.

Incubating time may vary. In different embodiments an incubation may lasts from approximately 3 seconds to approximately 3 min, e.g. around 10 seconds, 20 seconds, 30 seconds, 1 minute, 2 minutes, 5 minutes, 10 minutes. or longer, e.g. one-two hours, overnight. For example, incubating the sample in an aqueous solution comprising a binding agent ("binding agent media") may lasts 1-3 minutes.

Incubating may be performed at various temperatures, depending on the type of target, binding agent, etc, e.g. it may be performed at a temperature from around +4° C. to around +40° C.

In one embodiment, the invention relates to a binding agent comprising antibody or a derivative of an antibody. Accordingly, the binding agent media may be an aqueous medium in which the binding agent is soluble and stable and is capable of binding to its binding partner in the target site. It is typically a buffered aqueous solution that has pH in the range from 4 to 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. Other suitable buffers may be found in Good, N E., et al (1966) Hydrogen ion buffers for biological research. Biochem. 5(2), 467-477. The pH value of the media may be essential for binding of the binding agent to the binding partner; it may be optimized depending on the nature of the binding agent and the target.

In some embodiments the binding agent medium may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc. The amount of salt in binding agent media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

In some embodiments binding agent media may comprise an organic modifier (by the term "organic modifier" is meant any non water solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments binding agent media may comprise a detergent, e.g. polyethylenglycol-p-isooctyphenyl ether (NP-40» or a surfactant (e.g. selected from the surfactants based on polyoxyethylene sorbitanmonolaurate (TWEEN), or a surfactant based on block copolymers (PLURONIC etc.), etc. The amount of the detergent may vary from about 0.001% to about 5% /v/v or w/v).

In some embodiments binding agent media may comprise a binding agent stabilizing agent, e.g. bovine serum albumin or dextran. The amount of the stabilizing agent may vary from 0.01% to 20% (w/v).

In some embodiments binding agent media may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, binding agent media may comprise one or more blocking agents for saturating non-specific binding sites, i.e. sites of the solid support that do not comprise the target. Some non-limiting examples of blocking agents suitable for different embodiments may be the Denhard's solution, bovine serum albumin, skimmed milk, etc.

As discussed above, the invention contemplates a great variety of species of targets, binding agents and assay formats; accordingly, the composition of binding agent medium may vary and should be adjusted for every particular embodiment using the knowledge of the art.

Amounts of the binding molecules in a binding agent may vary depending on the species of said binding molecules, their affinity to the binding partner in the sample (or in target sites of the sample), species of the binding partner, sample species, composition of the media, etc. As discussed above, the amount of the binding agent in a media is predetermined to bind substantially all units of the binding agent partner present the sample. Depending on the affinity of the first and second binding molecules to the binding partner, the quantity of each in the binding agent may vary, however, according to the invention the amount of the binding agent (including both first and second binding molecules) should not be less, preferably higher than the value of Kd of binding agent-binding partner complex, preferably above this value, such as about 5-10% higher the Kd value, preferably more than 10% than Kd value such as about 11-14%, 15-20%, 20-25%, 25-50%, or more that 50% higher than the Kd value, such as 100% higher, 200% higher, e.g. 300%-1000% higher or more. The amount of the second binding molecule in the binding agent mixture may be above or below the corresponding value of Kd (i.e. second binding molecule-binding partner complex), however, in some embodiments it may be preferred that the amount of the second binding molecules in the mixture is higher of the Kd, at least 1% higher, such as 5% to 25% higher, 10-50% higher, 15-75% higher, etc. The amount of the first binding molecule may according to the invention be defined individually for different embodiments; in some embodiments it may be below of the Kd value of first binding molecule-binding partner complex, on other embodiments equal or above of the Kd.

Detection

A method of the invention may comprise one or more steps preceding or following the step of incubating of the sample with the binding agent of the invention in order to detect the detectable part of the first binding molecules in the sample.

The detectable part of the first binding molecule may comprises an optically detectable label, an enzyme, a member of a specific binding pair, a particle, a radioactive substance, a combination of any thereof. Accordingly, a label may be detected directly, i.e. by observing the label using means allowing the observation this detectable label, e.g. a microscope. For some detectable parts of the invention there are no appropriate detectable means exist, so these parts may be detected, so called, "indirectly, by using detecting agents capable of specifically detecting and making them "detectable", e.g. label the sites of the presence of the detectable parts of the first binding molecules with color or fluorescence or the like. In one embodiment, the detectable part may comprise a member of a specific binding pair.

Detecting of such detectable parts may comprise one or more steps of using binding agents which comprise the corresponding member of this specific binding pair. This detecting procedure may further comprise a step of visualization of the target site comprising the first binding agent, e.g. use an enzyme-mediated deposition of a reporter molecule at said target site. In one embodiment, the enzyme-mediated deposition is a horse-radish peroxidase (HPR) mediated deposition of a reporter. It may be any traditional HRP-DAB (3,3'-diaminobenzidine) labeling of the target sites well known in the art. A procedure recently described in WO2010094284, WO2010094283, WO201047680, or WO2012143010 (all references are incorporated herein by reference) May also be used. Some examples of visualization of target sites according the later procedures are described in Examples.

The HPR-mediated visualization of the detectable part of the first binding molecules is, in some embodiments, preferred visualization method, but not limiting, as any visualization procedure that that is suitable for detecting the detectable part of the first binding molecules in a sample of the invention may be used. This flexibility of applicable visualization procedures is one of the advantages of the method of the invention.

The detection procedure may also comprise one or more steps of blocking, washing, mounting, or the like.

The method of the invention may be used in an assay for evaluation of a target in a histological sample, wherein the assay comprises a step of detection of the target in the sample using a binding agent that have a specific affinity to the target. The method may practically be implemented into any such assay, both to those that already exist in the art or to those that will be developed in the art of evaluation of a target in a histological sample by use of target specific binding agents. Accordingly, as assay for evaluation of a target in a histological sample, comprising a step of detection of the target in the sample according to the present method is another aspect of the invention.

The assay comprising the target site detecting step of the invention may be both for qualitative and quantitative evaluation of the target in a sample. Both evaluations are embodiments of the assay of the invention. The assay of the invention may be used for a qualitative and/or quantitative evaluation of a biological marker, e.g. a biomarker of a disease. In one embodiment, the invention relates to a gene of the ErbB family of growth factor receptors, or a product of said gene as a biomarker of a disease, e.g. Her2, Her2, etc. In some embodiments, the biomarker may be a combination of two or more biomarkers which are capable of functioning as a single target unit in the context of the invention, e.g. the ErbB receptor dimmers or the like.

The method of the invention is comparable with automatic, semiautomatic or manual target detection and visualization methods and assays.

2. Kit-Of-Part

Another aspect of the invention relates to a kit-of-parts comprising a composition comprising a binding agent which is capable of specifically binding to the binding partner comprised in said one or more target sites, wherein the amount of the binding agent is sufficient to bind to substantially all units of the binding partner present in the sample, and wherein the binding agent is characterized in that it comprises first binding molecules and second binding molecules, wherein the first binding molecules comprise a binding part and a detectable part, and the second binding molecules comprise a binding part, wherein the binding part of both first and second binding molecules is capable of specifically binding to the binding partner and competing for said binding, and wherein the second binding molecules do not comprise a part that is substantially identical to the detectable part of the first binding molecules.

In different embodiments a kit-of-parts of the invention may further comprise one or more of the following
(i) reference materials;
(ii) reagents for detection and/or visualization of the detectable part of the first binding molecules;
(iii) protocols for detection and/or visualization of the detectable part of the first binding molecules;
(iv) protocols for target quantification;
(v) instrument(s) for visualization of a target and/or image capture or a reference to such instruments;
(vi) software for controlling the instruments;
(vii) software for image analysis;
(viii) locked image analysis algorithms;
(ix) standards for evaluating the samples, e.g. scoring standards and scoring guidelines;
(x) instructions for use.

All embodiments of the method of the invention regarding the binding agent, binding molecules, sample, media, target, visualization means, etc., are also embodiments of the kit-of-parts of the invention.

In particular, the binding agent of a kit-of-parts of the invention may comprise binding molecules that are members of any of specific binding pairs with the target in the sample or with a substance associated with the target (embodiments of all the latter are discussed above).

In one preferred embodiment the binding agent may comprise an antibody, or a fragment or a derivative thereof, in another embodiment, it may comprise a nucleic acid or a nucleic acid analog sequence.

In one embodiment, the first binding molecules and the second binding molecules of the binding agent may be antibodies that are (i) specific for the same antigen; (ii) capable of inhibiting each other binding to said antigen, and (iii) have different Fc regions; in another embodiment, the first binding molecule may be an antibody and the second binding molecule is the F(ab)2 fragment of the same antibody.

The kit-of-parts of the invention is, in a preferred embodiment, for evaluation of a target in a histological sample. In one preferred embodiment for quantitative evaluation of the target.

The target may be in different embodiments be a biological or chemical target molecule, particle, molecular or cellular complex, molecular or cellular structure, virus or microorganism, or a fragment of said target molecule, particle, complex, structure, virus or microorganism. In one preferred embodiment, the target is a biomarker of a disease, such as one of the discussed above.

In one embodiment, the kit-of-parts comprises a reference materials, such as one or more histological samples comprising cells with predetermined amounts of the target.

In one embodiment the kit-of-parts may comprise a binding agent comprising a mixture of the first and the second binding molecules, wherein the binding molecules are present in a predetermined ratio, characterized in that the amount of the second binding molecules is higher than the amount of the first binding molecules.

The above mentioned embodiments are not-limiting.

EXAMPLES

The following is a description of non-limiting working examples illustrating some embodiments of the disclosed invention. The theoretical considerations are part of the description and not bounding. The described embodiments are exemplary and not limiting.

Abbreviations

MBHA 4-Methylbenzhydrylamine
NMP N-Methyl Pyrolidon
HATU 2-(1h-7-azabenzotriazole-1-yl)-1,1,3,3 tetramethyl uronium hexafluorophosphate; methenamminium
DIPEA Dilsopropyl EthylAmine
DCM Dichloro Methane
TFA TriFluoroacetic Acid
TFMSA TriFluor Methyl Sulphonic Acid
Flu Fluorescein
Dex Dextran
HPLC High Performance Liquid Chromatography
equi. Equivalent
L30 1,10,16,25-tetraaza-4,7,13,19,22,28-hexaoxa-11,15,26,30-tetraoxo-triacontane
L60, L90, L120, L150 different polymers of L30, comprising 2, 3, 4 or 5 L30 reapeats
CIZ 2-chloroZ=2chloro Benzyloxycarbonyl
FITC FlouresceinIsoThioCyanate
HRP Horse Radish Peroxidase
GaM Goat anti-Mouse antibody
DNP 2,4 dinitro-fluorbenzene (DiNitroPhenyl)
ACim 4-amino-Cinnamic acid
LPR Liquid Permanent Red (Dako K0540)
Sin sinnapinic acid (4-hydroxy-3,5-dimethoxy cinnamic acid)
Caf caffeic acid (3,4-dihydroxy cinnamic acid)
Alpha-CHC apha-ciano-4-hydroxycinnamic acid
PNA-X peptide nucleic acid oligomer (N-(2-aminoethyl)-glycine) comprising different substituents coupled to the central nitrogen
A adenine-9-acetic acid,
C cytosine-1-acetic acid,
2,6-diaminopurine-9-acetic acid,
G guanuine-9-acetic acid,
Gs 6-thuioguanine-9-acetic acid,
P 2-pyrimidinone-1 acetic acid,
T thymine-1-acetic acid,
Us 2-thiouracil-1-acetic acid.
Dpr 2,3 diamino-propioninc acid,
Phe phenylalanine,
Tyr tyrosine,
Trp tryptophane,
Lys lysine,
Cys cysteine, betaala betaalanine, N,N diacetic acid
FFPE formaldehyde fixed paraffin embedded
SMD single molecule detection
Cross-linker a first substrate of an enzyme with oxidoreductase activity
Reporter a detectable molecule
RDM Reporter Deposition Medium
BAM Binding Agent Medium Materials and Protocols for Visualization of a Protein Target in Histological Sample (According to the Methods Described in WO2010094283, WO201047680, Both Incorporated by Reference).

1. Reporter Molecules:

1.1. Sin-Lys(Sin)-Lys(Sin)-L150-Lys(Flu) (0328-018/D21047/D21067)

Synthesis is performed solution phase following solid phase synthesis of intermediates carrying free N-terminal amino groups and free lysine side chains amino groups. Alpha-N-Boc-(epsilon-N-2-Cl-Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.

Boc-(Lys(2-Cl-Z))3-L150-Lys(Fmoc) is prepared on solid phase. The Fmoc group is removed, followed by fluorescein labeling as described above. The intermediate NH2-((Lys(NH2))3-L150-Lys(Flu) results from cleavage from resin. It is precipitated with diethyl ether, dissolved in TFA, precipitated then dissolved in NMP and made basic with DIPEA. This solution is mixed with an equal volume of 0.2 M sinnapinic acid (4-hydroxy-3,5-dimethoxy cinnamic acid) in NMP activated by HATU and DIPEA. After 10 min the labeling is complete and the crude product is further "scrubbed" by addition of ethylene diamine to a concentration of 10% for 5 minutes. Following precipitation with diethyl ether, the product is further dissolved in TFA and precipitated with diethyl ether three times to remove low molecular weight debris. Prior to "scrubbing" with ethylene diamine, mass spectroscopy shows two kinds of adducts (and combinations thereof): +(176)n indicating extra ferulic acids (phenolic esters on other ferulic acids and fluorescein) and +98 (N,N'-tetramethyl uronium adducts, likewise on unprotected phenolic groups). These are completely removed by the ethylene diamine treatment, and active esters and ferulic acid oligomers are likewise decomposed.

1.2. Fer-Lys(Fer)-Lys(Fer)-Lys(Fer)-L150-Lys(Flu) (D1 9185/D120068)

On 1 g of MBHA resin with standard solid phase chemistry Boc-Lys(2ClZ)-Lys(2ClZ)-$L_{150}$-Lys(Fmoc) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA:TFMSA:thioanisol:m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 μL DIPEA and dissolved directly in 2 mL 0.3 M Ferulic acid preactivated with 0.9 equi HATU and 2 equi DIPEA. After 10 min. the crude product was precipitated with diethyl ether, redissolved in 1350 μL NMP and 150 μL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Other suitable reporter molecules (second HRP substrate) are described in PCT/DK2010/000137 and incorporated herein by reference i.e. reporter conjugate molecules described on pages 86-100 of WO2011047680 (PCT/DK2010/000137).

2. Binding Agents:

2.1. Goat Anti-Rabbit Antibody Conjugated with Dex70 Conjugated with HRP (L348.111, Fractions 10-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 44 nmol Goat-anti-Rabbit 196 microL water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Rabbit (GaR) and HRP. The product was divided into 4 fractions based on conjugate size: The first two fraction containing product (Frac. 8-9) eluded as a first peak, presumably containing some cross linked conjugates, then followed by a broad shoulder that was divided into fractions 10-11 (homogeneous large conjugates) and fractions 12-21 (smaller variable conjugates) and finally unconjugated enzymes and antibodies in fractions 22-42. Measurements on individual product fractions, as well as fractions containing non-conjugated antibody and HRP, showed a total conjugate recovery of 87%; ratio dex:GaM:HRP=1:0.96:10.9.

2.2. Goat-Anti-Mouse-Dex70-HRP (D18033/D18175)

13.7 nmol divinylsulphone were activated 70 kDA MW dextran and reacted with 602 nmol HRP were in 600 microL buffer (100 mM NaCl, 25 mM NaHCO$_3$, pH 9.5) for 3 h at 30 C. Then 41.1 nmol Goat-anti-Mouse F(ab)$_2$ antibody in 105 microL water was added, and the reaction was continued for additional 16 h. The reaction mixture was quenched by addition of 70 microL 0.165M cystein for 30 min and the product was purified on superdex 200 in 100 mM NaCl, 10 mM HEPES pH 7.2. The eluded product was a Dextran conjugate comprising Goat-anti-Mouse (GaM) and HRP (Ratio dex:GaM:HRP=1:1.1:7.5).

2.3. Anti-HER2-Antibody Conjugated with Dex70 Conjugated with HRP (D21100, Fractions 9-10)

4.6 nmol 70 kDA MW dextran was reacted with 202 nmol HRP in 125 microliters of buffer A (100 mM NaCl, 25 mM NaHCO$_3$, pH 9.5) for 3 h at 30 C. Thereafter 18 nmol antiHer2 in 489 microL of water was added to the dextran-HRP conjugate and the mixture was allowed to react for further 21 h at 30 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiHer2 and HRP. The product was divided into 4 fractions based on conjugate size: The first two fraction containing product (Frac. 7-8) eluded as a first peak, presumably containing some cross linked conjugates, then followed by a broad shoulder that was divided into fractions 9-10 (homogeneous large conjugates) and fractions 11-19 (smaller variable conjugates) and finally unconjugated enzymes and antibodies in fractions 20-41. Measurements on individual product fractions, as well as fractions containing non-conjugated antibody and HRP, showed a total conjugate recovery of 68%. Assuming direct proportionality between incorporated HRP and Dextran showed that fractions 9-10 contained 9.1 HRPs and 0.6 antibodies per Dextran. Only these two fractions were used for experiments.

2.3. AntiFITC Antibody Conjugated with Dex70 Conjugated with HRP (AMM 353-022 Fractions 8-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 66 nmol antiFITC in 196 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiFITC and HRP. The product was divided into 3 fractions based on conjugate size: The first fractions (8-11) containing product eluded as a first peak, then followed by a broad shoulder (smaller variable conjugates, frac. 12-27) and finally unconjugated enzymes and antibodies in fractions 28-45. Measurements on individual product fractions, as well as fractions containing non-conjugated antibody and HRP, showed a total conjugate recovery of 90%. Assuming direct proportionality between incorporated HRP and Dextran showed that fractions 10-11 contained 11.7 HRPs and 0.80 antibodies per Dextran. Only these two fractions were used for experiments.

2.4 Other binding agents suitable for the purposes of present invention are described in PCT/DK2010/000137 and incorporated herein by reference, i.e. binding agent molecules described on pages 100-106 of WO2011047680 (PCT/DK2010/000137).

3. First Substrate

DAB, ferulic acid and alpha-ciano-4-hydroxycinnamic acid (alpha-CHC) were used as the first substrate at the following conditions:

|  | DAB | Ferulic acid | Alpha-CHC |
|---|---|---|---|
| Optimal amount (Range) | 0.14 mM (0.1 mM-less than1 mM) | 1.5 mM (0.5 mM to 5 mM) | 5 mM (1.5 mM and 15 mM) |
| Optimal H$_2$O$_2$ amount | 1.5 mM | 0.9 mM | 0.6 mM |
| Optimal deposition time | 5-10 min | 10-15 min | 10-15 min |
| Optimal second substrate | Contains Fer or Sin | Contains Sin | Contains Fer |
| Dot diameter | 3-4 microns | 3-4 microns | 2-3 microns |

Compared to DAB, dots of a similar diameter with ferulic acid were obtained when incubation time was doubled; with alpha-ciano-4-hydroxycinnamic acid the incubation time was as for DAB, however the dots were smaller (2-3 microns in diameter compared to 3-4 microns for DAB).

4. Incubation Media

Binding Agent Medium (BAM)

0.1% 4-aminoantipurine, 0.2% Procline 2% BSA, 0.2% Casein, 2% PEG, 0.1% 10 TWEEN20 (polyoxyethylene (20) sorbitan monolaurate), 0.1 M NaCL, 10 mM HEPES, pH 7.2. (ABCPT-buffer)

5. Reporter Deposition Medium (ROM):

50 mM imidazole HCl pH 7.5, 0.1% Nonidet P40, 0.1%, benzalkonium chloride, 0.005% (1.5 mM) hydrogen peroxide.

6. Other Reagents

DAB chromogen solution (Dako K3465)
LPR chromogen solution (Dako K0640)
Haematoxilin counterstain (Dako S3301)
Wash buffer (Dako 53306)
Target retrieval solution (Dako S1699)
Mounting media Dako Fairmount (S3025)

7. Instruments.

Dako Autostainer Classic. This instrument is a totally open and freely programmable automated NC instrument where reagents and incubation times can be used and set at will. The instrument performs four basic actions 1. Aspirate reagent.
2. Blow wash buffer off horizontally placed slide.
3. Dispense reagent onto slide. (Known as sip and spit.)
4. Wash a slide by flushing it with wash buffer.

A typical program for a single slide is described below in protocol 1 (see Example 1). For all SMD experiments the initial peroxidase block and the target visualization steps were kept invariable.

Example 1. Quantification of a Target in a Histological Sample. Determination of Kd1, Kd2 and Pr (Method I)

Theoretic Considerations:

In order to define a number of single entities of a target in a sample and, in particularly, total number of said units, e.g. single target protein molecules, several complex equilibrium experiments may be performed, employing:

1. Several Reference samples of a test material with identical, but unknown, levels of an immobilized protein molecules, Pr. (e.g. serial sections of a single block of homogeneous Her2 reference cells lines);
2. A primary antibody, Ab1 (e.g. a high affinity monoclonal Rabbit-anti-HER2) with unknown dissociation constant, Kd1 that binds to said protein,
3. An Enzyme labeled secondary antibody, Ab2 with unknown dissociation constant, Kd2, that binds to said primary antibody.
4. Technologies for visualizing almost every single molecule of said secondary antibodies as discrete visually distinguishable dots (termed herein "single molecule dots" or "SMD") (e.g. as described in PCT/DK2010/000137 or herein).

According to the present invention the level of immobilized target in a sample, e.g. a protein, can be expressed as counted SMD per nucleus (e.g. in reference cell lines samples), or per area or volume of a tissue sample, etc; the number of molecules can via Avogadro's Number be translated into concentration of said molecules in the sample.

It is generally accepted that theoretical framework for antibody protein interaction is a complex equilibrium. The antibody will reach equilibrium with the target protein:

$$Ab1+Pr \leftrightarrow Ab1{:}Pr \qquad \text{F1}$$

Governed by the dissociation constant, Kd1 of the antibody:

$$\frac{[Ab1] \times [Pr]}{[Ab1{:}Pr]} = Kd1 \qquad \text{F2}$$

Under such equilibrium conditions, total protein, PrTotal and total antibody, Ab1Total will be distributed between free protein and complex and free antibody and complex $$PrTotal = Pr + Ab1{:}Pr \qquad \text{F3}$$

$$Ab1Total = Ab1 + Ab1{:}Pr \qquad \text{F4}$$

From F2 follows:

$$[Pr] = \frac{[Ab1:Pr] \times Kd1}{[Ab1]} \quad \text{F5}$$

Substituting F5 into F3 gives:

$$PrTotal = \frac{[Ab1:Pr] \times Kd1}{[Ab1]} + [Ab1:Pr] \quad \text{F6}$$

F6 can then be rearranged as the following:

$$PrTotal = [Ab1:Pr] \times \frac{Kd1 + [Ab1]}{[Ab1]} \quad \text{F7}$$

The first experimental challenge lies in determining when this first equilibrium has been reached. [Ab1:Pr] can be detected and determined by a subsequent second equilibrium experiment with enzyme labeled Ab2 followed by SMD visualization. The first series of experiments, Exp1, can be used to establish that a sequential application of a constant concentration of Ab1 to samples with a constant amount of immobilized protein will eventually result in a constant amount of Ab1:Pr being detected in a subsequent second visualization step using enzyme labeled Ab2 and SMD detection.

The need to use multiple sequential additions of Ab1 arises from the fact that a single addition of Ab1 to a sample with immobilized protein will result in Ab1:Pr complex formation, and thus in a decrease in both Ab1 and Pr concentration. The first equilibrium may apparently be reached, but sequential additions of Ab1 to identical reference samples until a constant level of Ab1:Pr is detected must be used to access when a true equilibrium reflecting the concentration of Ab1 has been reached, i.e. when further additions of Ab1 will no longer result in an increase in Ab1:Pr being detected. A single or a few additions of Ab1 will result in equilibriums reflecting the total amount of protein in the immobilized samples rather than the concentration of Ab1. Ab1 will be depleted due to complex formation and the effective concentration in equilibrium will be significantly lower than the concentration of Ab1 applied.

Formula 4 reflecting the effects of lowered concentration of free antibody can be ignored, if multiple additions of antibody confirm that depletion or slow kinetics is not a case.

Experimental set-up to confirm the above theory may be designed as the following: A constant concentration of Ab1 is sequentially applied to samples with constant concentration of immobilized protein. The Ab1:Pr complexes formed are subsequently detected using an enzyme labeled secondary antibody and SMD visualization. Thus, a true equilibrium reflecting the concentration of Ab1, not the amount of immobilized protein, can be established. (The experiment confirming this theory is described below in Experiment 3a, which shows that, after four to five sequential 10 min-incubations reference samples with Ab1 no further increase in Ab1:Pr complexes is detected).

The theory behind the second complex equilibrium step is identical to the theory regarding the first (discussed above).

The second equilibrium is established between the enzyme labeled secondary antibody and the immobilized primary antibody protein complex:

$$\text{Ab1:Pr Ab2} \leftrightarrow \text{Ab2:Ab1:Pr} \quad \text{F8}$$

Governed by the dissociation constant, Kd2 of the labeled secondary antibody:

$$\frac{[Ab2] \times [Ab1:Pr]}{[Ab2:Ab1:Pr]} = Kd2 \quad \text{F9}$$

$$Ab1:PrTotal = Ab1:Pr + Ab2:Ab1:Pr \quad \text{F10}$$

$$Ab2Total = Ab2 + Ab2:Ab1:Pr \quad \text{F11}$$

From F9 follows:

$$[Ab1Pr] = \frac{[Ab2:Ab1:Pr] \times Kd2}{[Ab2]} \quad \text{F12}$$

Substituting F12 into F10 gives:

$$Ab1: PrTotal = \frac{[Ab2: Ab1: Pr] \times Kd2}{[Ab2]} + [Ab2: Ab1: Pr] \quad \text{F13}$$

F13 can then be rearranged into F14

$$Ab1: PrTotal = [Ab2: Ab1: Pr] \times \frac{Kd2 + [Ab2]}{[Ab2]} \quad \text{F14}$$

This second equilibrium can only be established, if the concentration of Ab1:Pr remains essentially constant during the second equilibrium experiment, i.e. that no significant dissociation between protein and primary antibody takes place during washing steps and incubation with enzyme labeled secondary antibody. If this condition is observed, it is possible to substitute Ab1:PrTota of Formula 14 for [Ab1:Pr] of Formula 7.

This gives the next equation (Formula 15):

$$PrTotal = [Ab2: Ab1: Pr] \times \frac{Kd1 + [Ab1]}{[Ab1]} \times \frac{Kd2 + [Ab2]}{[Ab2]} \quad \text{F15}$$

Formula 15 can be regarded as the theoretical foundation of the absolute count experiments, i.e. experiments where the total number of target molecules in a sample is determined, because it describes a relationship between Kd1 and Kd2, which can be determined in equilibrium experiments in connection with the antibody titrations, and the total protein concentration and complexes of the protein with the antibodies that are visualized as dots.

These experiments may be performed as the following: A constant concentration of Ab1 is sequentially applied to samples with constant concentration of immobilized protein. The Ab1:Pr complexes formed are subsequently detected using an enzyme labeled secondary antibody and SMD visualization. The enzyme labeled secondary antibody (a constant amount thereof) is likewise sequentially applied multiple times. The experiment confirming this theory (described in Experiment 3b) has shown that after four to five sequential 10 min-incubations of enzyme labeled Ab2 with reference samples previously equilibrated with primary antibody no further increase in formation of Ab2:Ab1:Pr complexes was detected, neither a decrease (potentially resulting from a significant protein-Ab1 dissociation during washing steps and establishment of the second equilibrium) was detected. Thus, a true equilibrium reflecting the concentration of immobilized protein, [Ab1] and enzyme labeled [Ab2] can be established confirming the equation of Formula 15.

For the same reasons as discussed for Formula 4, now Formula 11 may be ignored. The effects of lowered concentration of free secondary enzyme labeled antibody can be ignored if multiple additions of this antibody confirm that depletion or slow kinetics is not a problem.

Tissue samples with unknown protein concentration level may be routinely incubated with primary antibodies in order to determine said unknown protein concentration. This step may be followed by steps of incubation with enzyme labeled secondary antibody followed by, yet, extra steps of visualization.

As a rule, in routine IHC staining procedures only single incubations with primary and secondary antibodies are used, and a physical agitation, either uncontrolled (due to gravity, evaporation or wicking) or controlled by active stirring of reagents on the slide, is an established practice. However, using mixing and/or relative high concentrations of both primary and secondary antibody, pseudo equilibrium conditions may be reached by a single reagent application, resulting in reproducible results (this is how the well-known histological staining systems work now, e.g. Envision system). Consecutive additions of an antibody reagent (primary or enzyme labeled secondary) results in relative stable equilibriums, and thus can also act as a safeguard against antibody depletion and allow, in contrary to the traditional IHC staining, the precise evaluation of the amount of the target in an IHC sample.

As described in Experiments below, the necessity of use of low amounts of high affinity primary antibody arises from the low value of Kd1 of the Her2 clone tested in combination with the need to use concentrations below Kd1 in order to measure Kd1. For routine use concentration well above Kd1 may be used, reducing the need for multiple additions. In case of the secondary antibody, it is the need to reduce dot overlap that prevents use of higher concentration. At higher concentrations the overlapping dots may prevent an accurate dot count, at least when counting is done manually.

When the staining conditions leading to forming non-ovelapping SMDs are observed, the SMD can be counted as Pr, and, if PrTotal can be kept constant (e.g. in case of use of sequential sections of same reference material), experiments with varying [Ab1] and constant [Ab2] will allow determining Kd1; PrTotal and Kd2 will still remain unknown, but constant. This allows rearrangement of Formula 15 into Formula 16:

$$\text{Dots} = \text{Constant} \times \frac{[Ab1]}{Kd1 + [Ab1]} \quad \text{F16}$$

The Constant (C) reflects the value of PrTotal of the sample and the fraction of Ab1:Pr complexes that are detected in the second equilibrium reaction with constant [Ab2]. And it is the absolute number of Dots that can be detected under those conditions. The equation of F16 means that at high and increasing [Ab1] the number of Dots will approach, but never reach a constant level. At low and decreasing [AM] the number of Dots, which is a hyperbolic function of [Ab1], will approach a linear function of [Ab1].

The number of Dots as function of [Ab1] is a hyperbolic function, and Formula 16 is used to determine Kd1 by fitting experimental data correlating Dots with [Ab1] in experiments with constant reference material and constant [Kd2]. However, using sequential additions of Ab1 at concentrations close to Kd1 reproducibly allow accurate determination of Kd1 via an excellent fit to Formula 16.

Experimental set-up that allows determination of Kd2 is slightly more complex. The challenge is that concentrations of enzyme labeled secondary antibody that are close to Kd2 invariably will lead to formation of dots the number of which will be too high to count due to overlap problems. Use of a very low concentration of primary antibody and/or use of reference material with a low protein concentration would not be a solution, as a background from high concentrations of secondary antibody will give a very high background noise due to unspecific bound secondary antibodies, thus would not accurately reflect the protein concentration. This is further compounded by difficulties of establishing the equilibrium at very low primary antibody concentrations. An approach to overcome these challenges is to use both primary and secondary antibody in relative high concentrations, in case of the secondary antibody with concentrations around Kd2, and visualizing the bound secondary antibody by conventional IHC. By conventional IHC is meant that the enzyme labeled secondary antibodies are used to generate a brown deposit of 3,3'-diaminobenzidine (DAB), e.g. by using the Envision system, rather than SMD visualization. The intensity of such conventional DAB deposits is not linear and does not correctly reflect the quantity of molecules of a target in the sample, however the intensity of two deposits may be visually compared and determined to be of approximately of the same intensity. Indeed, this is how the IHC-staining results are at present interpreted: they are evaluated by comparing the intensity of the brown deposit in test samples and reference samples and follow the graphic or descriptive guidelines for the interpretation.

Using identical reference material, PrTotal (of F15) can be kept constant. If [Ab1] and [Ab2] are also constant, and Ab2:Ab1:Pr is visualized by conventional IHC as a brown deposit, the staining will be of constant intensity. Evidently, the intensity has to be within the dynamic range of conventional IHC so that variations in Ab2:Ab1:Pr are reflected in variable intensity of the brown deposit. IHC slides are normally scored on a scale: +0 (no color at all), +1 (weak intensity), +2 (moderate intensity), and +3 (highest intensity/brownish-black). In order to accurately reflects [Ab1:Ab2:Pr], the score should be within the +0.5 to +2.5 range, so that upwards or downwards variation is detected, and, preferably, within the +1 to +2 range, where the intensity variation as function of [Ab1:Ab2:Pr] is most pronounced and the background noise is minimal.

Having established a reference system in the desired dynamic range (i.e. within +1 to +2 and [Ab2] around [Kd2]) Experiment 3d (described below) is carried out using a lower constant concentration of Ab1, $[Ab1]_2$ with variable and increasing concentration of Ab2 relative to the initial reference experiment By increasing [Ab2], the concentration of [Ab2:Ab1:Pr] will at some point reach a level identical to the prior established reference level, resulting in an identical intensity of brown deposit. When the intensity of the brown DAB deposit is of identical intensity to the deposit formed with [Ab1]$_1$ and [Ab2], it is to be concluded that:

[Ab2:Ab1:Pr]$_1$=[Ab2:Ab1:Pr]$_2$

Thus, the identical staining levels have been reached by two different combinations of [Ab1] and [Ab2] and constant PrTotal. It follows to the equation:

$$\frac{Kd1+[Ab1]_1}{[Ab1]_1} \times \frac{Kd2+[Ab2]_1}{[Ab2]_1} = \frac{Kd1+[Ab1]_2}{[Ab1]_2} \times \frac{Kd2+[Ab2]_2}{[Ab2]_2}$$

As Kd1 is known, as well as [Ab1]$_1$ and [Ab1]$_2$ from experimental conditions, the equation may be reduced to Formula 17 (C1 and C2 are Constants):

$$C_1 \times \frac{Kd2+[Ab2]_1}{[Ab2]_1} = C_2 \times \frac{Kd2+[Ab2]_2}{[Ab2]_2} \quad F17$$

Dividing by C$_1$ gives:

$$\frac{Kd2+[Ab2]_1}{[Ab2]_1} = C_3 \times \frac{Kd2+[Ab2]_2}{[Ab2]_2} \quad F18$$

Formula 18 may be rearranged to allow isolation of Kd2:

(Kd2×[Ab2]$_2$)+([Ab2]$_1$×[Ab2]$_2$)=(C$_3$×Kd2×[Ab2]$_1$)+ (C$_3$×[Ab2]$_1$[Ab2]$_2$), which can be reduced to:

$$Kd2 = \frac{(1-C_3) \times ([AB2]_1 \times [Ab2]_2)}{(C_3 \times [Ab2]_1) - [Ab2]_2} \quad F19$$

Where C$_3$ (which is equal to C2/C1, see above) is defined by:

$$C_3 = \frac{(Kd1+[Ab1]_2) \times [Ab1]_1}{[Ab1]_2 \times (Kd1+[Ab1]_1)} \quad F20$$

C$_3$ relates to two hyperbolic functions on top of each other reflects a constant level of the brown staining that is derived from two different sets of experimental conditions: first, a reference level is established by reaching a first equilibrium reflecting [Ab1]$_1$ and [Ab2]$_1$; then, the same reference level is reached by using [Ab1]$_2$ and [Ab2]$_2$. Kd1 is known, Kd2 can thus be determined.

A reference level of the conventional staining intensity may be produced using [Ab1]$_1$ and [Ab2]$_1$. Using a different concentration of Ab1, [Ab1]$_2$ allows titration of [Ab2] until a level of identical staining intensity is reached by [Ab2]$_2$. This allows determination of Kd2 from Formula 19.

Returning to the original Formula 15, having determined Kd1 and Kd2, any SMD staining experiment fulfilling the proviso of reaching equilibrium in both steps and allowing an accurate SMD dot count, will allow determination of PrTotal in the reference sample(s) used.

Any reference sample, wherein PrTotal has been determined in this way, obtains a status of "absolute reference".

The absolute number of proteins (or any other immobilized target compound) in the immobilized sample has been counted and may be expressed in absolute terms such as molecules per area/volume/cell etc. depending on the nature of the immobilized sample.

Experimental Evidence

As a test material serial sections of pellets of formalin fixed paraffin embedded cell lines sk45, df45, df23 expressing Her2 were used (these cell lines will further be referred to as the 0+, the 1+ and the 3+ cell line, correspondingly). These cell lines are the 0+, 1+ and 3+ control material for FDA approved Dako HercepTest for breast cancer. Pellets of the cell lines were embedded in a single block of paraffin to provide sections where the every cell lines present. The choose of the test material reflects availability of the material (e.g. each single block provides hundreds of serial sections, the presence of three different cell samples on each test slide allows inter correlation between the results of one staining procedure of three different test samples).

Slides with FFPE sections of blocks containing the three cell lines (further referred as "slides") were deparaffinized by emersion in xylene (2×5 min) followed by 96% ethanol (2×2 min) and 70% ethanol (2×2 min). Then, the slides were washed with deionized water and transferred to Target retrieval solution, either the high pH solution (Dako S2375), diluted 10× (examples 1 and 2 with anti cytokeration) or low pH solution (Dako S1700) (see examples 10.3-10.8 below). The slides were then heated to boiling in a microwave oven (approx 5 min) and gently boiled for 10 min. Afterwards the slides were allowed to cool for min 20 min and then were transferred to a wash buffer (Dako S3006) diluted 10×.

Pan specific anti-cytokeratin antibody (Dako M3515, monoclonal mouse) was used both as concentrate and diluted solution. Antibody dilutions were made based on total protein concentration (indicated on each vial) and considering the molecular weight of the antibody (150 kDa/mol). This antibody is further referred as "anti-cytokeratin".

Anti-Her2 antibody was a monoclonal rabbit antibody (Dako clone 25-11-3). Dilutions were made based on calculated total protein concentration in a concentrated solution and the molecular weight of the antibody of (150 kDa/mol). The antibody is referred herein as "anti-HER2".

Staining Protocol 1

Peroxidase block, 5 min in Dako S2023

Wash (a) Formation of Target Sites:

Primary antibody,

Wash

HRP-Labeled secondary antibody,

Wash.

(b) Formation of Reporter Dot of Deposits at Target Sites

Incubation of samples (a) 10 minutes with 0.28 mM DAB and 5 µM reporter (D21047) in RDM.

Wash c) Detection of Dots of the Reporter Deposits at Single Target Sites

Anti-FITC-AP, 10 min, 20 nM D20036 in BAM

Wash

LPR, 10 min, Dako K0640

Wash d) Haemotoxylin Counterstain
Haematoxylin, 5 min
Wash with deionized water
f) Mounting Additional washes may be introduced into the automated protocol. The automated scheduler will keep overall protocol time at a minimum, by reducing duration of washing steps to a minimum; however, duration of washing steps will depend on loading of the instrument. If a single slide is programmed to be stained, a single washing step might be reduced to 20 seconds, while a full load of 48 slides significantly increase washing time. To keep this time variation minimal, 10 slides in average were stained in each run. Accordingly, washing step duration was kept approximately 2 min per step. Multiple washes following reporter deposition and incubation of the deposits with anti-FITC-AP assures a minimal LPR background staining. Despite of massive amplification (it is estimated that each red Dots derived from a single antibody-dextran-HRP molecule bound to the target comprise in average 100 billion molecules of LPR) there can virtually no background be detected.

Extra washing might be recommended in order to reach the highest level of amplification and lowest background staining, while reporter and reporter binding agent are used in relative high amounts.

Evaluation of Staining

Dot counting was initially performed manually, by visual inspection of stained slides and their images. Automated image analysis was performed using the freeware JMicrovision vs. 1.27. In an exemplary embodiment, LPR red Dots produced as described and haematoxylin stained nuclei were automatically counted. Automated counts were verified by visual inspection and manual counts. Segmentation and object abstraction could be based on hue alone in Hue, Saturation, Intensity, (HSI) color space, i.e. both intensity and saturation set to full 0-255 range. Dot hue was set to 188(violet)-255 and 0-16 (orange), nuclear hue to 76 (green) to 163 (blue). Dot-nuclear contrast was enhanced by over exposing red (1.2), neutral green (1.0) and under exposure of blue (0.56) during image capture performed on an Olympus BX51 microscope fitted with a DP50 5.5 Mpixel camera and CellD image capture software.

Experiment 1. Determination of Kd of
Anti-Cytokeratin Antibody 8 slides with FFPE sections+0, +1 and +3 cell lines were pretreated and stained as described above (see pretreatment and protocol 1).

The primary antibody (anti-cytokeratin), was applied for 20 min in varying concentrations as described in the table:

| Slide number | Concentration of M3115 in BAM |
|---|---|
| 1 | 40 nM |
| 2 | 33 nM |
| 3 | 25 nM |
| 4 | 20 nM |
| 5 | 13 nM |
| 6 | 10 nM |
| 7 | 5 nM |
| 8 | 2.5 nM |

The slides were then mounted with aqueous Faramount. 3 images of each cell line pellet on each slide were captured, red colored dots were manually counted in each image and the number of counted dots was compared to a theoretically calculated number of dots in the samples.

Presuming that one molecule anti-cytokeratin (cAb) is associated with one dot, the theoretical number of dots (Ndot) may be calculated using the following formula $$Nd = \frac{[cAB_c] \times Ndot_{max}}{Kd + [cAb]}. \quad \text{(Formula 1)}$$

Wherein [cAb] is the concentration of anti-cytokeratin antibody, and Kd is the dissociation constant of the anti-cytokeratin antibody, i.e. cAb, and $Ndot_{max}$ is a constant.

The constant named $Ndot_{max}$ means maximal number of dots and in the present content means that the number of dots approaches the maximum value when the used concentration of an antibody is significantly above its Kd value, i.e. when the anti-cytokeratin antibody are used in a concentration that is far beyond the Kd value.

This formula is derived from the formula for the dissociation constants for the primary and secondary antibodies with the prerequisite that the absolute concentration of protein in every test sample (i.e. samples of cells +0, +1 and +3, 8 slides of each cells line with different concentrations of the antibody as indicated in the table below) is constant and the concentration of the secondary antibody is kept unvarying between slides.

The table (1) shows the number of experimentally obtained and theoretically calculated dots for every sample 1-8 for all three test cell lines:

| Slide | Concentration of primary antibody nM | Dots counted and calculated, total of 3 images in +0 cell line | | Dots counted and calculated, total of 3 images in +1 cell line | | Dots counted and calculated, total of 3 images in +3 cell line | |
|---|---|---|---|---|---|---|---|
| | | counted | calculated | counted | calculated | counted | calculated |
| 1 | 2.25 | 165 | 170 | 318 | 316 | 376 | 389 |
| 2 | 5 | 293 | 292 | 445 | 542 | 627 | 667 |
| 3 | 10 | 384 | 411 | 731 | 765 | 879 | 941 |
| 4 | 13.3 | 487 | 458 | 920 | 851 | 1043 | 1048 |
| 5 | 20 | 502 | 518 | 968 | 962 | 1140 | 1185 |
| 6 | 25 | 581 | 547 | 1026 | 1015 | 1333 | 1250 |
| 7 | 30 | 669 | 567 | 1159 | 1054 | 1546 | 1297 |
| 8 | 40 | 629 | 595 | 1269 | 1106 | 1663 | 1361 |

By fitting the curves generated from the formula to the curves generated from the experimental data, approximate values of Kd1 and Ndot$_{max}$ can be determined. Thus, Kd1 was set to 7 nM, for all three calculated series, Ndot$_{max}$ to 700 (+0), 1300 (+1) and 1600 (+3).

A Kd value of 7 nM is in good agreement with experimental count across all three cell lines. In case of the +1 and +3 cell lines, calculated values are slightly below measured values for high concentrations of antibody. Anti-cytokeratin antibody M 3515 has a broad specificity and it recognizes several different cytokeratin subtypes. Theoretically, for each cytokeratin subtype the antibody may have a slightly different Kd since the surroundings the antigen may be different and it may influence the antibody binding. This explains a "non-perfect fit" with the hyperbolic curve. Furthermore, that some unspecific binding might take place at concentrations well above the Kd value.

Conclusion

The performed quantification can be considered to be precise because the results from experiments where different slides and different cell lines were used can be directly compared, i.e. dot staining pattern provides an easy and rapid digitalized quantitative evaluation of samples, i.e. by counting the visually distinct dots, e.g. 600 dots are easily distinguishable from 300 dots in another sample.

The Kd value of the used secondary antibody (D20168) is not known, and it has not been shown that an equilibrium is reached in this step of affinity binding, however control experiments did show that further incubation with primary antibody (prolonged incubation time and additional portions of antibodies) did not lead to significant increase in signal. Thus, if a constant fraction of primary antibodies is recognized by the secondary antibody during the experiment, the latter has no influence on the Kd measurement. Using multiple applications of secondary antibodies twice as many dots can be produced. In these applications maximal number of dots per slide (Ndot$_{max}$) is also doubled, but these does not influence measurement the Kd.

Experiment 2. Determination of Kd of a Second Binding Agent (Goat-Anti-Mouse-Dextran-HRP Conjugate (020168).)

This experiment was performed using conventional IHC stains (Dako Envision system).

Slides were pretreated as described, and subjected to the following staining protocol 2:
1. Peroxidase block, 5 min
Wash
2. Anti-Cytokeratin, 20 min in incubation media 1
Wash
3. HRP-labeled secondary antibody (D20168), 20 min in incubation media 1
Wash
4. DAB chromogen solution, 10 min
Wash
5. Haematoxilin stain, 5 min
Wash with water
Wash
Wash with de ionized water.

12 samples of each of the three cell lines (+0, +1 and +3) were divided in two series, wherein six slides of the first series were incubated with of 2.5 nM anti-cytokeratin antibody and further incubated with 6 different concentrations of D20168 (100 nM, 50 nM, 25 nM, 15 nM, 10 nM and 5 nM), and six slides of the second series were incubated with 10 nM anti-cytokeratin antibody and further incubated with 6 different concentrations of D20168 (100 nM, 50 nM, 25 nM, 15 nM, 10 nM and 5 nM). The slides of both series were than stained with DAB (as chromogen) and Haemotoxilin according to the above protocol.

For all three cell lines staining intensity increased with increasing concentration, but leveled off within the dynamic range of the NC staining (below a score of +2.5).

As expected, using a higher concentration of primary antibody resulted in higher intensities of staining. The staining of the slide treated with 2.5 nM anti-cytokeratin and 100 nM D20168 (further referred as slide A) (of each cell line) was compared to the staining of slides with 10 nM anti-cytokeratin (within each cell line). Two independent mock observers were used to estimate the intensity of staining. They found that for all three cell lines the intensity of staining of the slide A was identical to the intensity of staining of the slide treated with 10 nM anti-cytokeratin and 15 nM D20168 (slide B). Because of the reference material was constant (same cell line control slides) and approximately the same staining intensity was observed in slides treated with different amounts of the primary and secondary antibody. it was concluded that the number of Cytokeratin-anti-Cytokeratin-D20168 complexes present in slides A and B (within one cell line) was the same. Accordingly, the following equation could be used to calculate Kd (i.e. Kd2) of the secondary antibody of D20168:

$$Kd2 = \frac{(1 - C_3) \times ([Ab2]_1 \times [Ab2]_2)}{(C_3 \times [Ab2]_1) - [Ab2]_2}$$

Wherein $C_1$, $C_2$ and $C_3$; $[Ab1]_1$=2.5 nM, $[Ab1]_2$=10 nM, $[Ab2]_1$=100 nM, $[Ab2]_2$=15 nM, and wherein $C_3$ defined from the following equation:

$$C_3 = \frac{C_2}{C_1} = \frac{(Kd1 + [Ab1]_2) \times [Ab1]_1}{[Ab1]_2 \times (Kd1 + [Ab1]_1)}$$

Thus, Kd2 of D20168 was calculated to be 25 nM.

Experiment 3a: Establishment of Equilibrium Conditions for Primary HER2 Antibody Due to a low Kd (i.e. high affinity) value for the HER2 antibody clone tested, initial attempts to determine the Kd value by means similar to example 1 might give results that would not fit well with equilibrium conditions: a single application of a very low concentrations (100 pM) of the primary antibody may lead to formation of incomplete equilibrium. Therefore, in order to defined and secure conditions of the equilibrium conditions for the HER2 antibodies, sequential additions of the primary antibody were applied to the samples of all three lines. Slides treated with the lowest concentration (100 pM) of the antibody, where antibody depletion and incomplete equilibrium problems were expected to be most severe, were as well treated with two sequential additions of high concentrations of the secondary antibody, to compensate depletion in of the primary antibody step.

The staining was done according to protocol 1 with the specific concentrations, incubation times and number of sequential additions for the primary and secondary antibodies, as the following.

100 pM HER2 antibody, 1-6 sequential incubations, 10 minutes each:

| Slide number | Number of additions |
|---|---|
| 1 | 1 |
| 2 | 2 |
| 3 | 3 |
| 4 | 4 |
| 5 | 5 |
| 6 | 6 |

One wash followed each addition (prior to the following addition);
5 pM HRP-Labeled Goat-anti-Rabbit (L348-111 frac. 9-10), two sequential incubations, 10 min each.

Three images (10× magnification) of each +0 and +1 cell line samples were taken and the number of SMD dots per nucleus was counted. The +3 cell line samples were disregarded due to a very intensive staining which did not allow an accurate count the dots. The results are presented in Table 2 below:

| Additions of anti-HER2 | Dot/nuclei(0+) (Series 1 of FIG. 5) | Dot/nuclei(1+) (Series 2 of FIG. 5) |
|---|---|---|
| 1 | 0.158 | 0.407 |
| 2 | 0.258 | 0.665 |
| 3 | 0.305 | 1.031 |
| 4 | 0.42 | 1.309 |
| 5 | 0.532 | 1.536 |
| 6 | 0.532 | 1.513 |

From the results of the experiment it was concluded that at least 5 additions of the HER2 primary antibody solution, were the amount of the antibody is 100 pM, is required to avoid depletion and establish true equilibrium condition in the tested samples.

Experiment 3b: Establishment of Equilibrium Conditions for Secondary Antibody

To define the equilibrium conditions for the secondary antibody, a high concentration of the HER2 primary antibody was used in the first step of the procedure which would expected to give a high level of bound primary antibody to the target, and a series of applications of low concentration of the secondary antibody (L348-111, fractions. 9-10), where depletion of the antibody would be expected to be most sever, was performed in the second step of the procedure.

The staining was done according to protocol 1 with the specific concentrations, incubation times and number of additions for the primary and secondary antibodies described below:
500 pM HER2 antibody, 2 sequential additions, 10 min each; Wash
5 pM L348-111, 1-5 sequential additions, 10 min each:

| Slide number | Number of additions |
|---|---|
| 1 | 1 |
| 2 | 2 |
| 3 | 3 |
| 4 | 4 |
| 5 | 5 |

One wash was applied after each addition, prior to the following addition.

Three images (10× magnification) of each +0 and +1 cell sample were taken and the number of SMD dots per nucleus was counted. The +3 cell line samples were disregarded due to a very intensive staining which did not allow an accurate count the dots.

The results are presented in Table 3:

| Additions of Secondary antibody | Dots/nucleus (0+) (Series 1 of FIG. 6) | Dot/nucleus (1+) (Series 2 of FIG. 6) |
|---|---|---|
| 1 | 0.077 | 0.327 |
| 2 | 0.083 | 0.609 |
| 3 | 0.195 | 0.889 |
| 4 | 0.318 | 1.216 |
| 5 | 0.364 | 1.31 |

From the results of the experiment, it was concluded that at least 5 additions of 1.5 pM L348-111 frac. 9-10 was required to reach the equilibrium.

Experiment 3c: Determination of the Kd Value of the Anti-HER2

From examples 3a and 3b it has been known that 6 sequential additions of 100 pM HER2 antibody and subsequently 5 additions of 5 pM L348-111 were required in order to reach the equilibrium conditions and measure the Kd values. Accordingly, SMD staining of 12 slides of samples of the tree cell lines was performed according to protocol 1 with the specific concentrations, incubation times and number of additions for the primary and secondary antibodies as described below:
6 concentrations of the HER2 antibody, 6 sequential additions, 10 minutes each:

| Slide number | Concentration of HER2 |
|---|---|
| 1 and 2 | 100 pM |
| 3 and 4 | 200 pM |
| 5 and 6 | 300 pM |
| 7 and 8 | 400 pM |
| 9 and 10 | 500 pM |
| 11 and 12 | 1 nM |

One wash step was applied after each addition and prior to the following;
5 pM L348-111, 5 sequential additions, 10 min each.

Three images (10× magnification) of samples of each +0 and +1 cell lines were taken and the number of SMD dots per nucleus was counted. The +3 were disregarded due to very intensive staining, likewise, the slides incubated with the highest concentration of the primary antibody (1 nM).

The results of the experiment with samples of the +0 cell line are presented in Table 4:

| Concentration of Anti-HER2 | Theoretically calculated number of dots Kd 280, max 0.7 dot/nucleus (Series 1 of FIG. 7) | Dot/nucleus experimentally counted in 0+ cell line (Series 2 of FIG. 7) |
|---|---|---|
| 100 | 0.183246 | 0.186 |
| 200 | 0.290456 | 0.305 |
| 300 | 0.360825 | 0.358 |
| 400 | 0.410557 | 0.416 |

| Concentration of Anti-HER2 | Theoretically calculated number of dots Kd 280, max 0.7 dot/nucleus (Series 1 of FIG. 7) | Dot/nucleus experimentally counted in 0+ cell line (Series 2 of FIG. 7) |
| --- | --- | --- |
| 500 | 0.44757 | 0.451 |
| 1000 | 0.546022 | 0.69 |

Use of very low concentrations of both primary and secondary antibodies (100-500 pM and 5 pM correspondingly), combined with multiple sequential additions is necessary to reach the equilibrium conditions as demonstrated in experiments 3a and 3b. The 6 times addition of primary antibody at a concentration well above Kd (1 nM) should led to some background, which is expected, however the fit obtained from the 5 double determinations around Kd is very good.

Experiment 3d: Determination of Kd of Goat-Anti-Rabbit-Dextran-HRP Conjugate L348-111

This experiment was performed using conventional IHC stains. Slides were pretreated as described, and subjected to the following staining protocol 3:
1. Peroxidase block, 5 min
Wash
2. Anti-HER2 in incubation media 1, 6 additions, 10 min each;
Wash
3. L348-111 in incubation media 1, 3 additions, 10 min each;
Wash
4. DAB stain, 10 min
Wash
5. Haematoxilin stain, 5 min
Wash with water
Wash
Wash with de ionized water.

For each of the three cell line, three slides were stained (in triplicate) with 100 pM anti-HER2 and 50 nM L348-111. The other six slides were stained with 500 pM anti-HER2 and with decreasing concentrations of L348-111 (50 nM, 25 nM, 17 nM, 11 nM, 7.5 nM and 5 nM correspondingly). Two independent observes of the staining results found that for all three cell lines the intensity of the triplicate stain (100 pM anti-HER2 and 50 nM L348-111) was identical to the slide treated with 500 pM anti-HER2 and 11 nM L348-111. As the reference material was constant (same cell line control slides) and a constant staining intensity was observed, it could be concluded that the same number of HER2-anti-HER2-L348-111 complexes were present. Accordingly, the following formula was used to calculate the Kd of the secondary antibody:

$$Kd2 = \frac{(1-C_3) \times ([Ab2]_1 \times [Ab2]_2)}{(C_3 \times [Ab2]_1) - [Ab2]_2}.$$

Wherein $[Ab1]_1$ and $[Ab1]_2$ are two different concentrations of the primary antibody, and $[Ab2]_1$ nd $[Ab2]_2$ are different concentrations of the secondary antibody.

Calculating $C_3$ from the following equitation:

$$C_3 = \frac{C_2}{C_1} = \frac{(Kd1+[Ab1]_2) \times [Ab1]_1}{[Ab1]_2 \times (Kd1+[Ab1]_1)},$$

And using the values of $[Ab1]_1$=100 pM, $[Ab1]_2$=500 pM, $[Ab2]_1$=50 nM, $[Ab2]_2$=11 nM, Kd2 of L348-111 was found to be equal to 28 nM.

In the equilibrium titration of example 3c the results were fitted to 0.70 dots per nucleus (at conditions of saturation with primary antibody and use of L348-111 at 1.5 pM concentration). Accordingly, using the following equation it is possible to calculate the total amount of HER2 (PrTotal) present in +0 cells:

$$PrTotal = [Ab2 : Ab1 : Pr] \times \frac{Kd1+[Ab1]}{[Ab1]} \times \frac{Kd2+[Ab2]}{[Ab2]},$$

wherein [Ab2:Ab1:Pr] is the concentration of complexes HER2-anti-HER2-L348-111, Kd1 is the constant dissociation of anti-HER2, and Kd2 is the constant dissociation of L348-111, $[Ab1]_1$ nd $[Ab1]_2$ two different concentrations of the anti-HER2, and $[Ab2]_1$ and $[Ab2]_2$ are two different concentrations of L348-111.

Setting [Ab2:Ab1:Pr] at 0.70 SMD dots/nucleus, the first fraction to 1 and Kd2 to 28 nM and [Ab2] to 1.5 pM, the value of PrTotal is calculated to be 13.000 molecules/nucleus.

This value is in a good agreement with the data of the field (see, for example, David. G. Hicks, D. G. and Schiffhauer, L. Assessment of HER2 Status by immunohistochemistry: Routine Use of Controls for IHC Testing-Laboratory Medicine. 2011; 42(8):459-467) that the 0+ cell line express 21,600±6700 copies of the Her2 receptor on the surface of these cells.

Example 2. Quantification of a Target in a Histological Sample (Method II)

1. Theoretical Considerations

The method (II) for estimation of the total (absolute) number of target molecules in cells has a number of similar approaches compared to the method (I), however it has also some differences.

One of the problems associated with the previously described method is that equilibrium conditions should be established for both primary antibody and labeled secondary antibody. In case of high target concentrations this can be a problem as depletion of binding agents during incubations will occur and it will thus require multiple and prolonged incubations with the binding agents. The present method utilizes that using very high concentration of binding agents a "top" level of binding (which means that essentially all binding sites in the sample will be saturated with the corresponding binding agent) can be established without having the depletion problems. Evidently never 100%, but 90-99% binding of a protein target with a high affinity primary antibody, and 50-75% binding of the primary antibody with labeled secondary antibody may be reached. Within these ranges, experiments with a varying but high concentration of reagents can be used to establish more precise binding levels.

Further, using a mixture containing a high concentration of unlabeled secondary antibody and low concentration of labeled (the same) secondary antibody, equilibrium conditions can be reached, while only a small fraction of the primary antibodies bound to the target will be labeled.

The present method further utilizes the possibility provided by the present visualization method that labeled secondary antibody may be visualized in several ways, depending on degree of amplification. In case of low amounts of the target bound primary antibody, a labeled secondary (or a mixture of labeled and unlabeled) antibody can be used to produce countable dots. In case of high amounts of the target bound primary antibody, the same reagent (or mixture) can be used to produce a conventional stain. The experiment thus may comprise several steps:

1. Incubations with high concentrations of binding agents are used to establish equilibrium conditions leading to recognition of a high and known fraction of targets. Such experiments are carried out with both primary and labeled secondary antibody. Such conditions will further be referred to as "top level" conditions.

2. Then, a mixture of labeled secondary and unlabeled secondary antibody that recognizes an unknown fraction of primary antibodies is prepared and used for incubation of a tissue sample with a high target expression that has been treated with a primary antibody at the top level conditions. The incubation is followed by visualization of the bound labeled secondary antibody with a conventional stain.

3. Using conventional staining, titration of the target bound primary antibody by the labeled secondary antibody at the top level conditions is performed. The important point is that equilibrium conditions need not be established between the target and the primary antibody. It is sufficient that using constant test material (the constant test material refers to a test material wherein the amount of the target is constant), a reproducible amount of the target is recognized. At some low concentration of primary antibody, a staining intensity is obtained that is identical to the level of staining that observed in step 2.

4. Using a method for visualizing single molecules as dots (as described in the present invention), a mixture of labeled and unlabeled secondary antibody is used to access a fraction of the target recognized by the same low concentration of the primary antibody as in step 3, relative to the fraction of the target recognized by the top level conditions of primary antibody.

5. Using the low level of primary antibody as of step 3, and the mixture of labeled and unlabeled secondary antibody as of step 2, single molecules are stained as dots and the number of dots per nucleus is evaluated.

From these experiments, the absolute number of targets can be determined. From experiments of steps 1 and 4, it is known which fraction of the target is recognized by the low concentration of the primary antibody. From experiments of steps 1 and 3, it is possible to deduce which fraction of the primary antibodies is recognized by the mixture of labeled and unlabeled secondary antibody used in experiment 2. We use the fact that the identical conventional staining levels are obtained in experiments of step 2 and 3 (which means that there is the identical number of the bound labeled secondary antibodies in the samples). Thus, we now know both the fraction of the target molecules recognized by the low concentration of the primary antibody, and the fraction of the primary antibodies recognized by the mixture of labeled and unlabeled secondary antibody of experiment in step 5. Multiplying these two factors gives the fraction of target molecules visualized as dots (see description of Experiment 1c below). As we further have counted the number of dots per nucleus, we know the number of target molecules present per nucleus. Thus, an absolute count has been performed.

2. Experimental Evidence

Materials and methods used in the following experiments, if not specifically disclosed, are as described above.

It is established that the Kd of the primary anti-Her2 antibody is 280 pM. (See experiment 3c) Using the antibody under equilibrium conditions (multiple additions until no further increase in signal is observed) at a concentration of 13.3 nM will result in labeling of 13.3 nM/(13.3 nM+0.28 nM) which is equal to approximately 97.9% of the primary target molecules.

Likewise, it is established that the Kd of the labeled secondary antibody is 28 nM. (See experiment 3d). Using the labeled secondary antibody under equilibrium conditions (multiple additions until no further increase in signal is observed) at a concentration of 25 nM will result in labeling of 25 nM/(25 nM+28 nM) which is equal to approximately 47.1% of the bound primary antibodies.

Experiment 1a

As constant test material was used serial sections of pellets of formalin fixed paraffin embedded cell lines. The cell lines used were 3+ control material from Dako HercepTest.

Slides with FFPE sections of blocks containing the cell lines, from now on referred to as "slides" were de paraffinized by emersion in xylene (2×5 min) followed by 96% ethanol (2×2 min) and 70% ethanol (2×2 min). The slides were washed with de ionized water and transferred to low pH target retrieval solution (Dako S1700). The slides were then heated to boiling in a microwave oven (approx 5 min) and then gently boiled for 10 min. The slides were allowed to cool for min 20 min before being transferred to wash buffer, Dako S 2343.

The slides were then stained on the Autostainer using the following protocol:

Peroxidase block, Dako S2023, 5 min
Wash
Several sequential 10 minute additions of 13.3 nM anti-HER2 primary antibody
Wash
Several sequential 10 minute additions of 100 pM Goat-anti-Rabbit-Dextran-HRP (L348.111) mixed with 5 nM unlabelled Goat-anti-Rabbit.
Wash
DAB (Dako K5007), 10 min
Wash
Haematoxylin (Dako S3301), 5 min
Wash with water
Wash
Results:

Three 10 minute additions of 13.3 nM antiHER2 were sufficient to reach equilibrium conditions. A fourth addition did not lead to increased staining level. Two 10 minute additions of 100 pM Goat-anti-Rabbit-Dextran-HRP (L348.111) mixed with 5 nM unlabelled Goat-anti-Rabbit was sufficient to reach equilibrium conditions. A third addition did not lead to increased staining level. The maximum staining level reached corresponded to approx. +1. (Although this cell line is referred to as +3, the use of low concentration of labeled secondary antibody mixed with a high concentration of unlabeled secondary antibody leads to labeling of a small fraction of primary antibodies).

Experiment 1b

Slides were pretreated as in Experiment 1a, and subjected to the following protocol (conventional DAB staining):
  Peroxidase block, Dako S2023, 5 min
  Wash
  10 minutes anti-HER2 primary antibody in varying concentration in the range 30 to 50 pM.
  Wash
  Two sequential 10 minute additions of 25 nM Goat-anti-Rabbit-Dextran-HRP (L348.111). A control slide showed that a third addition did not lead to increased signal.
  Wash
  DAB (Dako K5007), 10 min
  Wash
  Haematoxylin (Dako S3301), 5 min
  Wash with water
  Wash
  Results:
  An incubation with 40 pM anti-HER2 for 10 minutes resulted in a staining intensity (+1) identical to the maximum staining level reached in experiment 1a. The 43 pM incubation resulted in a visibly higher staining intensity, whereas the 37 pM incubation gave a visibly lower staining intensity.

Experiment 1c

The slides were pretreated as in experiment 1a and subjected to the following protocol (SMD staining):
  Peroxidase block, 5 min with Dako S2023
  Wash
  AntiHER2 primary antibody. Either 3 sequential 10 minute additions of 13.3 nM (slide 1) or one 10 minute addition of 40 pM (Slide 2-5)
  Wash
  Two sequential 10 minute additions of 500 femtoM Goat-anti-Rabbit-Dextran-HRP (L348.111) mixed with 5 nM unlabelled Goat-anti-Rabbit (slide 1-3) or two sequential 10 minute additions of 100 pM Goat-anti-Rabbit-Dextran-HRP (L348.111) mixed with 5 nM unlabelled Goat-anti-Rabbit (slides 4-5)
  Wash
  FITC-Reporter deposit: 10 min with incubation media 2 with 0.28 mM DAB and 10 microM D21067.
  Three washes
  Anti-FITC-AP: 10 min incubation, 20 nM D20036 in BAM
  Three washes
  LPR 10 min with Dako K0640
  wash
  Haematoxylin (Dako S3301), 5 min
  Wash with water
  Wash
  The slides were subjected to image analysis. Images of the entire cell pellets were captured at 20× (appprox. 300×300 nm pixels) using a ScanScope (Aperio) slide scanner. The images were analyzed using JMicrovision vs. 1.27 software. Red dots were identified in Intensity, Hue, Saturation color space as (I=0-234, H=187-37, S=52-255), blue nuclei were identified as (I=0-201, H=148-221, S=0-190). A size threshold was further applied to dots, objects bigger than 30 pixels were counted as two dots, objects bigger than 45 pixels were counted as three dots. A lower threshold of 100 pixels was applied to nuclei to filter away debris and smaller fragments of nuclei.

Note that the partially overlapping color spaces allow identifying individual pixels as both part of a red dot and as part of a nucleus, consistent with the dark violet appearance of dots on top of nuclei.

Results and Conclusions:

| Slide | Dots | Nuclei | Dots/nucleus |
| --- | --- | --- | --- |
| 1 | 56918 | 12388 | 4.59 |
| 2 | 151 | 13817 | 0.0109 |
| 3 | 177 | 13925 | 0.0127 |
| 4 | 52011 | 13618 | 3.82 |
| 5 | 61040 | 12939 | 4.72 |

Comparison of slide 1 to the average of slides 2 and 3 shows 388 times less bound primary antibody. As slide 1 represents around 97.9% (the value is derived from Kd1 of anti-Her2) of bound target molecules, application of 40 pM primary antibody for 10 minutes on the same test material (slides 2 and 3) gives rise to 1 in 396 target molecules being bound to the primary antibody (or 0.252%).

This data can now be used to analyze the results of Experiments 1a and 1b.

As mentioned, application of 40 pM primary antibody for 10 minutes results in labeling of 0.252% of the primary target. Subsequently, binding 47.1% (the value is derived from Kd of the secondary antibody) of the bound to the target primary antibodies to the secondary antibody results in 0.119% of the target being (indirectly) bound to the secondary antibody. This corresponds to Experiment 1c, i.e. using 40 pM primary antibody for 10 min. This must also be the case (as staining levels are identical) for Experiment 1 b, where the 13.3 nM primary antibody incubation (97.9% of primary targets bound) was followed by the incubation with the mixture of 100 pM labeled secondary antibody with 5 nM unlabeled secondary antibody. Thus, it can be concluded that the use of this mixture leads to 0.119%/0.979=0.121% of the primary antibodies being bound to the labeled secondary; 0.121% of 0.252% of the target is equal to 3.06 ppm (parts per million). Accordingly, the 4.27 dots (in average) per nucleus observed in slides 4 and 5 count to 1.395.000 target molecule per nucleus (this follow from the following calculation: 4.27/0.00000306=1.395.000).

The precision of this evaluation can be made by comparing slide 2 and 3 with slides 4-5. There were observed 362 times more dots (in average) using the mixture with 100 pM labeled secondary (slides 2-3) antibody than with 500 fM (slides 4-5). As the mixture with 100 pM results in 0.121% primary antibodies being labeled, the mixture with 500 fM must lead to 362 times lower labeling the target with antibody, i.e. 0.121%/362=3.34 ppm. It can be calculated that the level of labeling of target molecules in this slide: 97.9% of 3.34 ppm gives 3.27 ppm, and the observed 4.59 dots per nucleus corresponds to 1.402.000 target molecules per nucleus (4.59/0.00000327=1.402.000).

Example 3: Use of a Binding Agent Comprising a Mixture of First Binding Molecules and Second Binding Molecules Experiment 1. Binding Agent Comprising a Mixture of a Rabbit-Anti-her2 with a Mouse-Anti-her2 Specific for the Same Epitope 8 Slides with FFPE sections of mamma carcinoma with HercepTest™ Intensity score between 1+ and 2+ were de-paraffinized in xylene and ethanol and epitope retrieved in PT-Link (Dako) at 97 degrees for 20 min in 10 mM HEPES pH 8.0 with 0.1% NP-40.

The slides were then stained according to the following protocol (A) on the Autostainer (Dako):
  (a) Peroxidase block, 5 min in Dako S2023
  Wash
  (b) Incubation with the binding agent:
  A mixture of the first binding molecule Rabbit-anti-Her2 (Monoclonal Rabbit anti-Human HER2, clone DAK-HcT-2:DG44) and the second binding molecule Mouse-anti-Her2 (Monoclonal Mouse anti-human Her2 antibody clone DAK-H2-384, F11, G4, C9)
  Wash
  (c) Detection of the first binding, molecule:
    Incubation with HRP-Labeled secondary antibody against Rabbit-anti-Her2
    Wash.
    Deposition of a reporter molecule (Reporter Fer-Lys (Fer)-Lys(Fer)-Lys(Fer)-L150-Lys(Flu) (D19185/D120068)
  (d) Detection of the reporter at target sites
    DAB, 2×5 min, Dako K0640
    Wash
  (e) Haemotoxylin counterstain
    Haematoxylin, 3 min
    Wash with deionized water
  (f) Mounting By mixing Rabbit-anti-Her2 antibody with the Mouse-anti-Her2 antibody specific for the same epitope, the portion of targets bound to the Rabbit-anti-Her2 antibody was manipulated by changing the ratio between the Rabbit-anti-Her2 and Mouse-anti-her2 while retaining equilibrium conditions. Thus, the signal intensity was also be manipulated since the anti-Rabbit HRP conjugated detection layer detect only Rabbit-anti-Her2 antibodies bound to Her2, but not Mouse-anti-Her2 antibodies bound to Her2

The slides were treated with mixtures of the Rabbit-anti-Her2 and Mouse-anti-Her2 having the ratios shown in the Table:

| Slide number | Rabbit-anti-Her2 (ng/ml) | Mouse-anti-her2 (ng/ml) |
| --- | --- | --- |
| 1 | 200 | 0 |
| 2 | 200 | 50 |
| 3 | 200 | 100 |
| 4 | 200 | 200 |
| 5 | 200 | 300 |
| 6 | 200 | 400 |
| 7 | 200 | 800 |
| 8 | 200 | 1600 |

The slides were analyzed and scored within the intensity score range from 0 no intensity to 4 high intensity. The results are presented in the table below.

| Slide number | Intensity results |
| --- | --- |
| 1 | 1.8 |
| 2 | 1.6 |
| 3 | 1.6 |
| 4 | 1.4 |
| 5 | 1.4 |
| 6 | 1.4 |
| 7 | 1.2 |
| 8 | 1 |

From the results of the experiment it was concluded that a mixture of Rabbit-anti Her2 and Mouse anti-Her2, can be used to adjust the signal intensity while keeping the reaction at equilibrium conditions.

Experiment 2. Binding Agent Comprising a Mixture of Monoclonal Rabbit-Anti-Her2 with f(ab)$_2$ Fragment of the Antibody The staining of 4 slides of mamma carcinoma with a HercepTest™ score of 2+ pretreated and immunostained as above (Experiment 1, protocol A) using the binding agent comprising a mixture of monoclonal Rabbit-anti-Her2 (see Experiment 1) with the f(ab)$_2$ fragment of the antibody. Specific concentrations were as indicated in the Table below.

| Slide number | Rabbit-anti-Her2-HRP conjugated (ng/ml) | with f(ab)$_2$ fragmentized Rabbit anti-Her2. |
| --- | --- | --- |
| 1 | 500 | 0 |
| 2 | 500 | 1000 |
| 3 | 500 | 1500 |
| 4 | 500 | 2000 |

Images of the slides were captured with Aperio Scanscope. The images were analyzed with ISH-vs. 1.2 software from Indica Labs. The slides where assessed and an intensity score was evaluated (ranging from 0 no intensity to 4 high intensity). The results are presented in the Table below:

| Slide number | Intensity results 0 = none, 4 = high |
| --- | --- |
| 1 | 2.2 |
| 2 | 1.8 |
| 3 | 1.6 |
| 4 | 1.6 |

From the results of the experiment it is concluded that a mixture of Rabbit-anti Her2 and the f(ab)$_2$ fragment of the antibody can be used to adjust the signal intensity while keeping the reaction at equilibrium conditions.

Experiment 3. Binding Agent Comprising a Mixture of Labeled and Unlabeled Antibodies (First and Second Binding Molecules)—Visualization of the First Binding Molecule in the Target Site According to WO2012143010 (Incorporated by Reference)

18 Slides with FFPE sections of Her2+1 control cell lines were de-paraffinized in xylene and ethanol and epitope retrieved in PT-Link (Dako) at 97 degrees for 20 min in 10 mM HEPES pH 8.0 with 0.1% NP-40.

The slides were stained according to the following protocol on the Autostainer (Dako):
  1. Peroxidase block, 3% hydrogen peroxide, 10 min. Wash Dako S3006.
  2. Monoclonal Rabbit-Anti-Her2 antibody, 6.6 nM in incubation media 1 (Tris:HCl 50 mM pH 7.6, NaCl 0.3 M, Bovine Serum Albumin 2%, Bronidox, 0.02%, 4-aminoantipyrine 2.44 mM, PolyEthyleneGlycol MW 3.000 3%, Caseine 0.05%, TWEEN 20 (polyoxyethylene (20) sorbitan monolaurate) 0.1%), 20 min. Wash Dako S3006.

4. 9 slides were again treated with the Goat-Anti-Rabbit-Dextran70-HRP, 200 fM+unlabelled Goat-Anti-Rabbit in varying concentrations in the incubation media, 20 min. Wash Dako S3006. (identical to step 3) The other 9 slides were not subjected to this step.
5. 2 microM reporter D19185/D120068, 5.3 mM alpha-CHC, 0.59 mM hydrogen peroxide in 50 mM in imidazole:HCl pH 6.8, 10 min. Wash Dako S3006.
6. Anti-FITC-Alkaline phosphatase, 40 nM in Media 1, 10 min. Wash Dako S3006.
7. Liquid Permant Red, Dako K0640, 10 min. Wash Dako S3006.
8. Haematoxilin counter stain, Dako S3301, 5 min. Wash with water, wash Dako S3006.

The slides were dehydrated in 99.9% ethanol for 1 min and cover slipped with Tissue-Tek Film cover slipper (Sakura).

Images of the slides were captured with Aperio Scanscope. The images were analyzed with ISH-vs. 1.2 software from Indica Labs. Settings were adjusted to detect blue nuclei (Red 0.650, Green 0.704, Blue 0.291) and red dots (Red 0.072, Green 0.952, Blue 0.296). While these two types of objects show almost identical transmission of blue light (Blue=0.291 vs. 0.296) the nuclei had low transmission of both red and green (0.650 and 0.704) while the red dots were had very high transmission of red and very low transmission of green (0.072 and 0.952). This provided unequivocal (as confirmed by visual inspection) identification of nuclei and dots. To further enhance correct identification of the membrane localized red dots, a logic filter was applied so that only dots within 5 microns of a nucleus were counted. On each slide around 15.000 cells were counted to assure statistically valid data. The results are summarized in the table below:

| Concentration of unlabeled Goat-anti Rabbit in steps 3 and 4 | 0 nM | 3 nM | 10 nM |
| --- | --- | --- | --- |
| Average of three slides subjected to step 3 only | 0.134 dots/cell | 0.073 dots/cell | 0.033 dots/cell |
| Average of three slides subjected to step 3 and 4 | 0.242 dots/cell | 0.087 dots/cell | 0.036 dots/cell |
| Increase in Dot/cell by step 4 | 81% | 19% | 9% |

Results and Discussion:

As shown in other examples, when using low concentrations of a binding agent alone, multiple additions are required to reach equilibrium. In this example a 81% increase is observed by the second addition of Goat-anti-Rabbit-Dex-HRP, showing that a single addition is far from sufficient to reach a stable equilibrium. In contrast, when using a mixture of labeled and unlabelled binding molecules, significantly fewer dots marking the target sites are detected by a single addition, yet a second addition leads only to small increase in dot number. Comparing 2 binding agent comprising 3 nM and 10 nM unlabeled binding molecules, it may be drawn the conclusion that the higher the concentration of the unlabeled binding molecules, the fewer binding sites comprising the target are visualized (i.e. fewer dots are detected) by single addition and the smaller the increase in the visualized target sites by a second addition.

The fact that fewer dots are detected, and even fewer are further detectable by a second addition, using mixtures of labeled and unlabeled binding molecules directed to the same target, shows that saturation of the target by the binding molecules takes place. Thus, the assay has been transformed from an equilibrium measurement (as of the Example 1 and Example 2 described above), that requires multiple additions of the binding agent or prolonged time to reach stable equilibrium conditions, to a competitive saturation assay where the target can be essentially saturated by a single addition of mixture of labeled and unlabeled molecules of one and the same binding agent. This is evidently advantageous, as the procedure is significantly faster, less laborious and much more robust with regard to minor fluctuations in time, temperature, reagent quality, instrumentation or human operator variation. Such competitive saturation assays don't preclude assays that measure immobilized targets in absolute terms, i.e. a target concentration per cell or volume of immobilized sample. As equilibrium experiments with primary antibody and labeled secondary antibody on constant test material, i.e. a specific cell line, can be used to determine absolute target concentration in that cell line, other assays using a mixture of a "detectable" and "non-detectable" binding agents can be calibrated against the constant test material, i.e. if it has been determined that a given cell line has 50.000 units of the target per cell, and a robust saturation assay with labeled-unlabeled binding agent produces 0.10 dots/cell (1 dot corresponding to one single unit (see for explanation WO20110476680 or WO2012062318, incorporated herein by reference), it can be concluded that that the assay detects 1 target unit in a sample comprising 500.000 target units.

Experiment 4: Binding Agent Comprising a Mixture of Labeled and Unlabeled Antibodies (First and Second Binding Molecules)—Visualization of the First Binding Molecule in the Target Site by Conventional HRP-DAB Stain (Envision™)

6 Slides with FFPE sections of Her2+0, +1, +2 and +3 control cell lines were de-paraffinized in xylene and ethanol and epitope retrieved in PT-Link (Dako) at 97 degrees for 20 min in 10 mM HEPES pH 8.0 with 0.1% NP-40.

They were then stained according to the following protocol on the Autostainer (Dako):
1. Peroxidase block, 3% hydrogen peroxide, 10 min. Wash Dako S3006.
2. Monoclonal Rabbit-Anti-Her2 antibody, 6.6 nM in Media 1 (see above), 20 min. Wash Dako S3006.
3. Goat-Anti-Rabbit-Dextran70-HRP(D18033/D18175), 25 nM+unlabelled Goat-Anti-Rabbit in varying concentrations (0, 8, 13, 21, 34 and 55 nM) in Media 1, 20 min. Wash Dako S3006.
4. DAB, K5007 Dako, 5 min. Wash Dako 53006.
5. Haematoxilin counter stain, Dako 53301, 5 min, Wash with water, wash Dako S3006.

After the staining the slides were dehydrated in 99.9% ethanol for 1 min and cover slipped with Tissue-Tek Film cover slipper, (Sakura).

Images of the slides were captured with Aperio Scanscope. The images were analyzed using "Membrane vs. 9.0" from Aperio. The original settings from Aperio were used, with the sole exception that "membrane completeness" was reduced from 50% to 20%. This feature adjusts the degree of membrane completeness required for a cell to be scored as +3. This reduction gave a better separation between +2 and +3 cells as virtually all intense cells scored +3 with 20% completeness requirement, whereas a 50% completeness requirement only lead to around 50%+3 cells even in case of very intense stains.

The algorithm has three basic outputs:
1. An Intensity score based on average of the membrane intensity staining. The dynamic range in case of the cell lines is from around 35 (very intense membranes) to 170-180 (no membrane stain).
2. A "Histoscore". Based on membrane intensity, cells are binned as either +3, +2, +1 or +0. The score is calculated as (% of +3×3)+(% of +2×2)+(% of +1×1)+(% of +0×0). The dynamic range is thus from 300 (all cells+3) to 0 (all cells+0).
3. A categorical score. Based on the Histoscore distribution the entire sample (cell pellet) is classified as either +3, +2+1 or +0. In (rare) cases of extremely homogenous material; i.e. all cells are of same category, the categorical score is identical to the Histoscore. In most cases what decides the categorical score is the "rule of 10%". This implies that if more than 10% of the cells are +3, the score will be +3, if more than 10% of the cells are +2 (but less than 10% are +3), the score will be +2, if more than 10% of the cells are +1 (but less than 10% are +2 or +3), the score will be +1, otherwise (less than 10% are +1, +2 or +3) the score will be +0.

The results of the evaluation of the 4 different cell lines and the binding agent comprising 6 different concentrations of unlabelled Goat-anti-Rabbit antibody are summarized in the Table below: I=intensity, H=Histoscore and C=categorical score.

| [GaR] | +3 cell line | +2 cell line | +1 cell line | +0 cell line |
|---|---|---|---|---|
| 0 nM | 38(I), 297(H), +3(C) | 67(I), 294(H), +3(C) | 123(I), 157(H), +3(C) | 176(I), 47(H), +1(C) |
| 8 nM | 39(I), 298(H), +3(C) | 77(I), 290(H), +3(C) | 139(I), 131(H), +3(C) | 172(I), 27(H), +1(C) |
| 13 nM | 39(I), 298(H), +3(C) | 79(I), 277(H), +3(C) | 148(I), 124(H), +2(C) | 176(I), 10(H), +0(C) |
| 21 nM | 44(I), 298(H), +3(C) | 89(I), 274(H), +3(C) | 164(I), 94(H), +2(C) | 177(I), 4(H), +0(C) |
| 34 nM | 49(I), 298(H), +3(C) | 101(I), 251(H), +3(C) | 180(I), 62(H), +1(C) | 174(I), 1(H), +0(C) |
| 55 nM | 51(I), 298(H), +3(C) | 110(I), 230(H), +3(C) | 182(I), 40(H), +1(C) | 175(I), 0(H), +0(C) |

Discussion of Results:

Each of the three scoring output represents different mathematical "views" of the same image, neither one the complete picture. It is, however, clear that without addition of unlabeled Goat-anti-Rabbit, the staining level is excessively intense with little discrimination between (especially) the +3 and +2 cell lines. Further the +1 is categorized as +3 and the +0 as +1.

The best results are obtained with either 34 nM or 55 nM unlabeled Goat-anti-Rabbit. All cell lines, except the +2, are given the correct categorical score and discrimination between these two cell lines is readily possible via the values of intensity or histoscore. Indeed, the histoscore discriminates readily between all four cell lines with 34 nM or 55 nM unlabeled Goat-anti-Rabbit, whereas intensity score is of little value for very weakly stained cells as cell morphology, and intensity of haematoxilin counter stain subtly effects membrane intensity.

Figure 2:
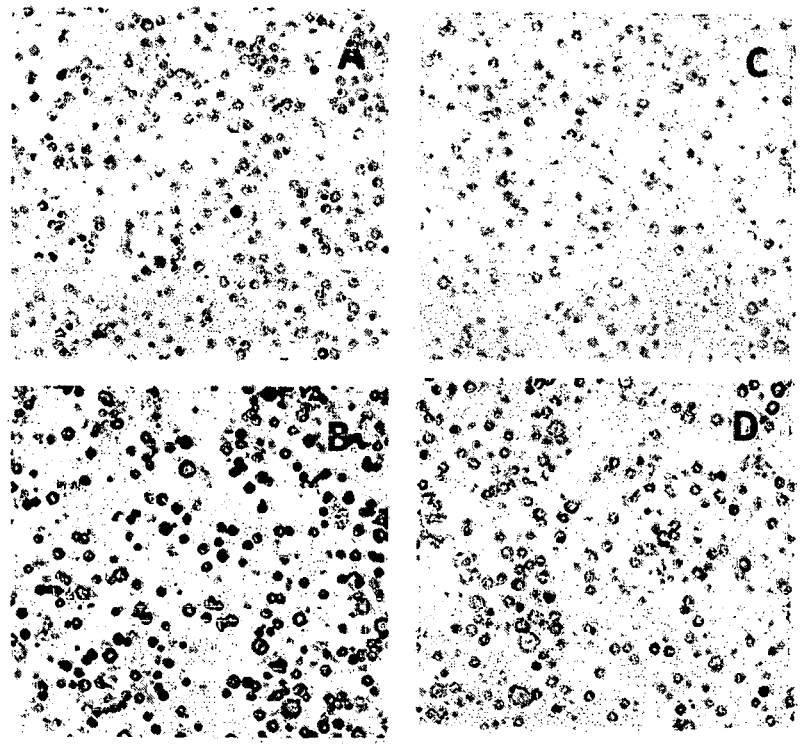
FIG. 2 shows representative images of Her2 1+ (A and C) and 2+ (B and 0) 30 positive cells immunostained for Her2 using HRP-OAB visualization system (Envision™) and scored according to HercepTest™, where the samples were incubated with a binding agent that consisted of only first binding molecules of the invention (A and B) and a binding agent that contained both the first binding molecules and second binding molecules (C and D). The corresponding target detection and visualization procedures are described in Example 3: Experiment 4.

Illustrative examples of the signal intensity attenuation by addition of unlabelled Goat-anti-Mouse are provided in FIG. 2.

The invention claimed is:

1. A method for detecting a target in a target site on one or more cells in a histological sample, wherein the target site comprises a binding partner for a binding agent, comprising,
    (a) incubating the sample presumably comprising the target in one or more target sites in an incubation medium comprising the a binding agent that is capable of specifically binding to the binding partner comprised in said one or more target sites on one or more cells,
        wherein the amount of the binding agent in the incubation medium is sufficient to bind to at least 51% of the binding partners present in the sample, and
        wherein the binding agent comprises a population of first binding molecules and a population of second binding molecules,
        wherein the first binding molecule comprises a binding part and a detectable part, and the second binding molecule comprises a binding part,
        wherein the binding part of the first binding molecule and the binding part of the second binding molecule are both capable of specifically binding to the binding partner and competing against each other for said binding,
        wherein the first binding molecule comprises an antibody molecule, or a derivative thereof, comprising an Fc region, and
        wherein the second binding molecule does not comprise a part that can be detected by a detector of the detectable part of the first binding molecule and the second binding molecule does not comprise the Fc region of the first binding molecule; and
    (b) detecting the detectable parts of the first binding molecules of the binding agent on one or more cells in the sample.

2. The method of claim 1, wherein the binding partner is the target or a substance associated with the target.

3. The method of claim 1, wherein the binding agent and the binding partner are members of a specific binding pair.

4. The method of claim 1, wherein the antibody molecule, or a derivative thereof, is specific for an epitope comprised in the binding partner, and
    the second binding molecule comprises an antigen binding portion that is specific for the same epitope as said antibody or is capable of inhibiting the first binding molecule binding to said epitope.

5. The method of claim 1, wherein the detectable part of the first binding molecule comprises an enzyme, an optically detectable label, a member of a specific binding pair, a particle, a radioactive substance, or any combination thereof.

6. The method of claim 1, wherein detecting the detectable parts of the first binding molecules comprises one or more steps.

7. The method of claim 1, wherein the target is a gene of the ErbB family of growth factor receptors, or a product of said gene.

8. The method of claim 1, wherein the target is a protein or a nucleic acid.

9. The method of claim 1, wherein the target is a biomarker of a disease.

10. The method of claim 1, wherein the binding partner is a polypeptide, and the second binding molecule is a F(ab)2 fragment of antibody capable of specifically binding to the binding partner.

11. The method of claim 1, wherein the second binding molecule is an F(ab)2 fragment.

12. The method of claim 1, wherein the first and second binding molecules each comprise an antibody or an antigen-binding portion of an antibody, and the target comprises an antigen.

13. The method of claim 12, wherein the binding part of the first binding molecule and the binding part of the second binding molecule comprise an antigen binding part of the same antibody or antigen binding parts of two different antibodies that are specific for the same binding partner.

14. The method of claim 1, wherein the concentration of the binding agent in the incubation medium is greater than the Kd (dissociation constant) value of the binding agent-binding partner complex.

15. The method of claim 14, wherein the concentration of the second binding molecules is equal to or greater than the Kd value of the second binding molecule-binding partner complex.

16. The method of claim 1, comprising a step of visualization of the target site using an enzyme-mediated deposition of a reporter molecule at said target site.

17. The method according to claim 16, wherein the enzyme-mediated deposition is a horse-radish peroxidase mediated deposition of a reporter molecule.

18. A method for detecting a target in a target site in a histological sample, wherein the target site comprises a binding partner for a binding agent, comprising
   (a) incubating the sample presumably comprising the target in one or more target sites in an incubation medium comprising the a binding agent that is capable of specifically binding to the binding partner comprised in said one or more target sites,
   wherein the amount of the binding agent in the incubation medium is sufficient to bind to at least 51% of the binding partners present in the sample, and
   wherein the binding agent comprises a population of first binding molecules and a population of second binding molecules,
   wherein the first binding molecule comprises a binding part and a detectable part, and the second binding molecule comprises a binding part,
   wherein the binding part of the first binding molecule and the binding part of the second binding molecule are both capable of specifically binding to the binding partner and competing against each other for said binding,
   wherein the first binding molecule comprises an antibody molecule, or a derivative thereof, comprising an Fc region, and
   wherein the second binding molecule does not comprise a part that can be detected by a detector of the detectable part of the first binding molecule and the second binding molecule does not comprise the Fc region of the first binding molecule;
   (b) counting the detectable parts of the binding agent of the first binding molecules in the sample; and
   (c) determining a quantity of the target in the sample.

19. The method of claim 18, where the method comprises determining an absolute quantity of the target.

20. The method of claim 18, where the method comprises determining a relative quantity of the target.

* * * * *